(12) United States Patent
Liu et al.

(10) Patent No.: US 10,738,076 B2
(45) Date of Patent: Aug. 11, 2020

(54) LANOSTEROL PRODRUG COMPOUND AND PREPARATION METHOD THEREFOR AND USE THEREOF

(71) Applicant: ZHONGSHAN OPHTHALMIC CENTER, SUN YAT-SEN UNIVERSITY, Guangzhou, Guangdong (CN)

(72) Inventors: Yizhi Liu, Guangzhou (CN); Yandong Wang, Guangzhou (CN); Xiaolin Li, Shanghai (CN); Zhi Luo, Shanghai (CN); Liang Shen, Shanghai (CN); Lijuan Hou, Shanghai (CN); Xinxin Wen, Shanghai (CN); Haiying He, Shanghai (CN); Jian Li, Shanghai (CN); Shuhui Chen, Shanghai (CN)

(73) Assignee: ZHONGSHAN OPHTHALMIC CENTER, SUN YAT-SEN UNIVERSITY, Guangzhou, Guangdong (CN)

( * ) Notice: Subject to any disclaimer, the term of this patent is extended or adjusted under 35 U.S.C. 154(b) by 0 days.

(21) Appl. No.: 16/346,111

(22) PCT Filed: Jan. 25, 2018

(86) PCT No.: PCT/CN2018/074120
§ 371 (c)(1),
(2) Date: Apr. 29, 2019

(87) PCT Pub. No.: WO2018/137683
PCT Pub. Date: Aug. 2, 2018

(65) Prior Publication Data
US 2019/0256548 A1  Aug. 22, 2019

(30) Foreign Application Priority Data

Jan. 25, 2017 (CN) .......................... 2017 1 0061039
Sep. 22, 2017 (CN) .......................... 2017 1 0868274

(51) Int. Cl.
*C07J 9/00* (2006.01)
*A61P 27/12* (2006.01)
(Continued)

(52) U.S. Cl.
CPC .............. *C07J 9/00* (2013.01); *A61K 9/0048* (2013.01); *A61K 9/08* (2013.01); *A61K 31/575* (2013.01);
(Continued)

(58) Field of Classification Search
CPC ........................................................ C07J 9/00
See application file for complete search history.

(56) References Cited

U.S. PATENT DOCUMENTS 8,815,485 B2 *  8/2014  Tanaka ................. C07C 251/78
                                                       106/496
2007/0015740 A1    1/2007  Keown et al.
2016/0096864 A1    4/2016  Savage et al.

FOREIGN PATENT DOCUMENTS

CN    104058993 A    9/2014
CN    105902515 A    8/2016
(Continued)

OTHER PUBLICATIONS

Dikusar et al., Chemistry of Natural Compounds (Translation of Khimiya Prirodnykh Soedinenii) (2003), 39(2), 186-190 CODEN: CHNCA8; ISSN: 0009-3130.*

(Continued)

*Primary Examiner* — Paul V Ward
(74) *Attorney, Agent, or Firm* — Foley & Lardner LLP

(57) ABSTRACT

Disclosed are a lanosterol prodrug compound, a pharmaceutically acceptable salt and an isomer thereof, and a pharmaceutical composition comprising the lanosterol prodrug compound and the use thereof in the preparation of a drug for treating cataracts. The lanosterol prodrug compound has a better permeability than lanosterol.

(Continued)

-continued

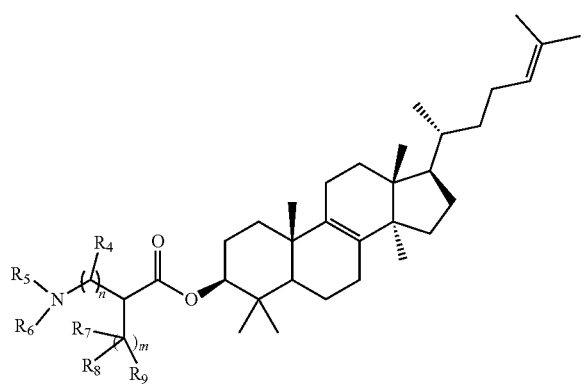
(III)

13 Claims, 3 Drawing Sheets

(51) Int. Cl.
*A61K 9/00* (2006.01)
*C07J 41/00* (2006.01)
*C07J 43/00* (2006.01)
*A61K 9/08* (2006.01)
*A61K 31/575* (2006.01)

(52) U.S. Cl.
CPC .......... *A61P 27/12* (2018.01); *C07J 41/0055* (2013.01); *C07J 43/003* (2013.01)

(56) References Cited

FOREIGN PATENT DOCUMENTS

| CN | 106074568 | A | | 11/2016 | |
|---|---|---|---|---|---|
| EP | 2803672 | A1 | | 11/2014 | |
| JP | S62120398 | A | | 6/1987 | |
| JP | H0930953 | A | | 2/1997 | |
| JP | H0967226 | A | | 3/1997 | |
| JP | 2012046640 | | * | 3/2012 | |
| JP | 2014205659 | A | | 10/2014 | |
| RU | 2283318 | C1 | | 9/2006 | |
| WO | 2013105523 | A | | 5/2015 | |
| WO | 2016029197 | A1 | | 2/2016 | |
| WO | 2016029199 | A1 | | 2/2016 | |
| WO | WO2016029197 | | * | 2/2016 | .............. C12Q 1/60 |
| WO | 2019097434 | A1 | | 5/2019 | |

OTHER PUBLICATIONS

Meth-Cohn et al., Journal of the Chemical Society, Chemical Communications (1986), (9), 695-7.*
International Search Report and Written Opinion of PCT/CN2018/074120 dated Apr. 19, 2018.
L.Zhao et al., "Lanosterol reverses protein aggregation in cataracts", Nature, 2015, vol. 523, No. 7562, p. 607-611.
B.Testa et al., Hydrolysis in Drug and Prodrug Metabolism Chemistry, Biochemistry and Enzymology (Book contents).
Database CA [online] CAS, STN database accession No. 1989:574521, 1989, CAS No. 123191-87-7, 123212-62-4, 123212-63-5.
Database CA [online] CAS, STN database accession No. 1997:329000 ( see JPH0967226).
H.Wieland et al., "Über die Nebensterine der Hefe. IV.Kryptosterin", 1937, vol. 529, p. 68-83 (relevant paragraph with English translation).
W. M. Stokes et al., "The separation of the compounds of the lanosterol group present in "isocholesterol" by chromatography of the p-iodobenzoates-l/\1/\3/\1 and benzoates", Archives of Biochemistry and Biophysics, 1957, vol. 67, No. 2, p. 272-279.
E. A. Dikusar et al., "Synthesis of some terpene-alcohol, sterol, and plant phenol esters of 4,5-dichloroisothiazol-3-carboxylic acid", Chemistry of Natural Compounds, 2003, vol. 39, No. 2, p. 186-190.
H. Kaneko et al., "Substrate specificity for formation of cholesterol ester conjugates from fenvalerate analogues and for granuloma formation", Xenobiotica, 1988, vol. 18, No. 1, p. 11-19.
Registry (STN) [online], Jul. 27, 2008, CAS No. 1036372-64-1.
A. P. Gray et al., "Steoid antifertility agents. Ionic complexes of basic derivatives for prolonged action", Journal of Medicinal Chemistry, 1978, vol. 21, No. 7, p. 712-715.
Extended European Search Report issued in counterpart European application No. 18744021.9 dated Oct. 25, 2019.
First Examination Report issued in counterpart Australian application No. 2018212270 dated Nov. 26, 2019.
First Office Action issued in counterpart Japanese application No. 2019-552560 dated Dec. 16, 2019.

* cited by examiner

LANOSTEROL PRODRUG COMPOUND AND PREPARATION METHOD THEREFOR AND USE THEREOF

CROSS-REFERENCE TO RELATED APPLICATIONS

The present application is the U.S. National Stage Entry of PCT international application No. PCT/CN2018/074120, filed Jan. 25, 2018, which claims priority of the Chinese patent application No. CN201710061039.8 filed on Jan. 25, 2017 and the Chinese patent application No. CN201710868274.6 filed on Sep. 22, 2017, the contents of which are incorporated herein by reference in their entireties.

TECHNICAL FIELD

The present invention relates to a compound represented by formula (I), (II) or (III), a pharmaceutically acceptable salt and an isomer thereof, and a use thereof in manufacturing a medicament for treating ophthalmic diseases.

BACKGROUND

Cataract is a disease of the eye which occurs in the lens in the eyeball and the lens turbidity is collectively called cataract. Aging, heredity, metabolic abnormality, trauma, radiation, poisoning and local malnutrition can cause damage to the lens capsule resulting in increase of permeability and lose of barrier function, or cause metabolic disorders of the lens resulting in denaturation of lens protein and formation of turbidity. If the lens of the eyeball changes from transparence to opacity and has an impact on the sunlight received by eyes, it will affect the eyesight of the eyes. When the degree of turbidity of eyeball is light, the effect on vision is lighter, but as the degree of turbidity gradually deepens, the visual acuity will increase, and severe cases will lead to blindness. Cataract is one of the most common eye diseases leading to blindness and it is a major cause of blindness. Since the mechanism of cataract formation is still unclear, no breakthrough has been made in drug therapy. Therefore, currently the only effective treatment is surgical treatment.

Although the continuous improvement of cataract surgery has provided great assistance to the treatment of cataract, the cure rate of surgical treatment is still far below the incidence rate, and there is the possibility of serious complications. On the other hand, the cost of surgical treatment of cataract is very high, and even in developed countries, cataract imposes a huge burden on the medical insurance system. Therefore, the prevention and treatment with usage of drugs play a decisive role. At present, therapeutic drugs available clinically for cataract include: 1, aldose reductase inhibitors, such as cataline (catalin, kary uni, prifenoxinesodium), phacolysin, bendazac L-lysine, etc.; 2, anti-oxidative damage drugs, such as glutathione, taurine, aspirin, etc.; 3, nutrient metabolism drugs, such as vitamins, carotenoids, etc.; 4, chinese herbal compound including Shihu Yeguang Pill, Qiju Dihuang Pill, Shijueming San and so on. It has been confirmed by long-term clinical trials that these drugs for the treatment of cataract can only delay the deterioration of cataract, but can not reverse the condition to treat cataract. Meanwhile, as China begins to enter an aging society, the number of cataract patients is increasing, and the demand for cataract drugs will become more urgent. Therefore, new varieties of ophthalmic external anti-cataract drugs with safety, good curative effect, strong intraocular penetration and stable nature are needed clinically.

Lanosterol is an amphiphilic molecule enriched in the lens which is synthesized from lanosterol synthase (LSS) through a key cyclization reaction of the cholesterol synthesis pathway and can reduce the abnormal aggregation of lens proteins and make it regularly rearranged to restore crystal transparency. Studies have shown that lanosterol synthase can be detected in the lens. Furthermore, in the Shumiya cataract rat study, a specific combination of homozygous mutations of lanosterol synthase and farnesyl diphosphate farnesyltransferase 1 (FDFT1) can alleviate cholesterol levels in the lens and cause cataracts. Meanwhile, our recent studies have found that lanosterol can significantly reduce pre-formed lens protein aggregates in vitro at the cellular level. It has also been confirmed that lanosterol can reverse the condition of cataract and bring about clarification and transparency of the lens in vivo. This result has recently been published in Nature and attracted worldwide attention and it is a new molecule for the prevention and treatment of cataract.

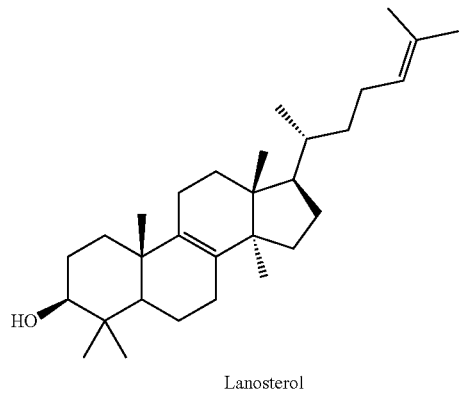 [SMILES: CC(C)=CCC[C@@H](C)[C@H]1CC[C@@]2(C)C3=C(CC[C@]12C)[C@@]1(C)CC[C@H](O)C(C)(C)C1CC3]

Lanosterol

Kary uni eye drops is a medicine produced by Santen Pharmaceutical Co., Ltd in Japan for the treatment of early senile cataract and the structural formula of its active ingredient is showed below:

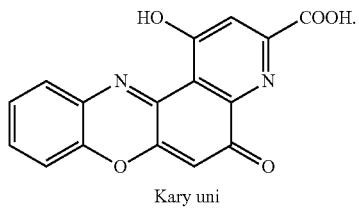 [SMILES: O=C(O)c1cc(O)c2c3nc4ccccc4oc-3cc(=O)c2n1]

Kary uni

SUMMARY OF THE PRESENT INVENTION

The present invention provides a compound represented by formula (I), (II) or (III), a pharmaceutically acceptable salt or an isomer thereof,

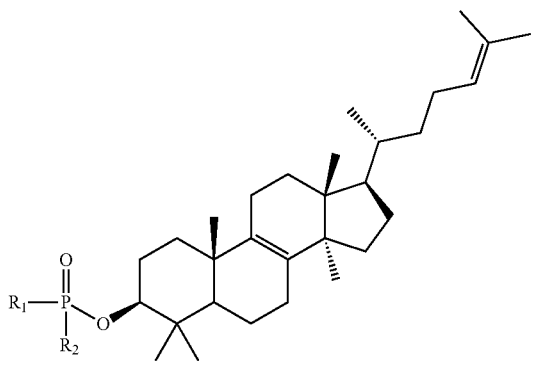

(I)

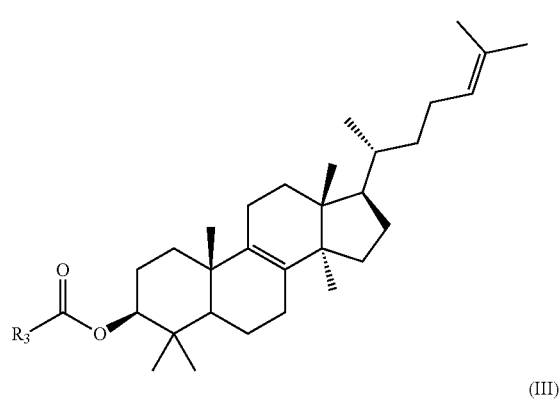

(II)

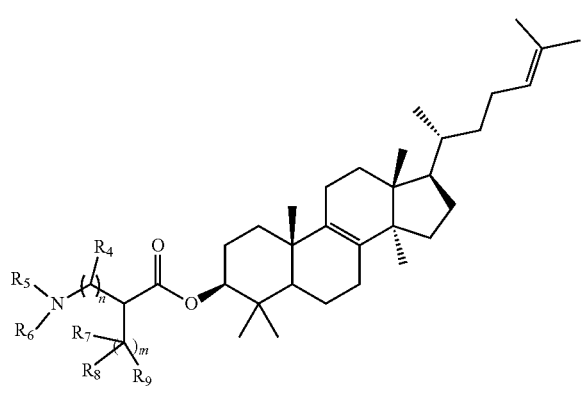

(III)

wherein, m is 0 or 1, when m is 0, the moiety

is absent;

n is 0 or 1;

$R_1$ is $C_{1-3}$ alkyl-O—C(=O)—$C_{1-3}$ alkyl-NH— which is optionally substituted with 1, 2 or 3R;

$R_2$ is selected from the group consisting of phenyl-O— and 5-10-membered heteroaryl, each of which is optionally substituted with 1, 2 or 3 R;

$R_3$ is selected from the group consisting of 6-10-membered aryl, 6-10-membered aryl-$C_{1-3}$ alkyl-, 5-10-membered heteroaryl and 5-10-membered heteroaryl-$C_{1-3}$ alkyl-, each of which is optionally substituted with 1, 2 or 3 R, but $R_3$ is not phenyl and

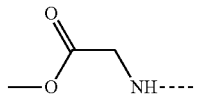

$R_4$ is H, F, Cl, Br, I, OH or $NH_2$, or $R_4$ is $C_{1-6}$ alkyl which is optionally substituted with 1, 2 or 3 R;

$R_5$ is H, or $C_{1-6}$ alkyl which is optionally substituted with 1, 2 or 3 R;

$R_6$ is H, or $C_{1-6}$ alkyl which is optionally substituted with 1, 2 or 3 R;

$R_7$ is H, F, Cl, Br, I, OH, COOH, $CONH_2$, $NH_2$, SH or $NH_2C$(=NH)NH—, or $R_7$ is selected from the group consisting of $C_{1-6}$ alkyl, $C_{1-6}$ heteroalkyl, phenyl and 5-10-membered heteroaryl, each of which is optionally substituted with 1, 2 or 3 R;

or $R_7$ and $R_6$ are linked together to form a 3-10-membered ring which is optionally substituted with 1, 2 or 3 R;

or $R_7$ and $R_4$ are linked together to form a 3-10-membered ring which is optionally substituted with 1, 2 or 3 R;

or $R_4$ and $R_6$ are linked to $R_7$ to form a 3-10-membered ring which is optionally substituted with 1, 2 or 3 R;

$R_8$ is H or $C_{1-3}$ alkyl;

$R_9$ is H or $C_{1-3}$ alkyl;

each of R is independently F, Cl, Br, I, $NH_2$, $NO_2$, OH, CN, COOH or $NH_2C$(=NH)NH—, or selected from the group consisting of $C_{1-3}$ alkyl and —C(=O)O—$C_{1-3}$ alkyl, each of which is optionally substituted with 1, 2 or 3 R';

R' is F, Cl, Br, I, $NH_2$, $NO_2$, OH, CN or COOH;

the "hetero" in the 5-10-membered heteroaryl or $C_{1-6}$ heteroalkyl is independently selected from the group consisting of —NH—, N, —O— and —S—;

in any of the above cases, the number of heteroatom or heteroatom group is independently 1, 2 or 3.

In some embodiments of the present invention, each of R is independently F, Cl, Br, I, $NH_2$, $NO_2$, OH, CN, COOH, $CH_3$, $NH_2C$(=NH)NH—, $CH_3CH_2$—, $CF_3$ or —O—C(=O)—$CH_3$, and other variables are as defined in the present invention.

In some embodiments of the present invention, $R_1$ is

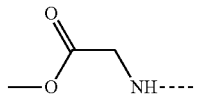

which is optionally substituted with 1, 2 or 3 R, and other variables are as defined in the present invention.

In some embodiments of the present invention, $R_1$ is

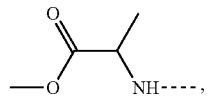

and other variables are as defined in the present invention.

In some embodiments of the present invention, $R_2$ is

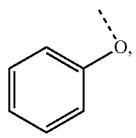

and other variables are as defined in the present invention.

In some embodiments of the present invention, $R_3$ is selected from the group consisting of phenyl, thienyl, pyridyl, quinolyl, pyrimidyl, isoxazolyl and 1,2,4-oxadiazolyl, each of which is optionally substituted with 1, 2 or 3 R, but $R_3$ is not phenyl and

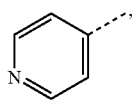

and other variables are as defined in the present invention.

In some embodiments of the present invention, $R_3$ is selected from the group consisting of

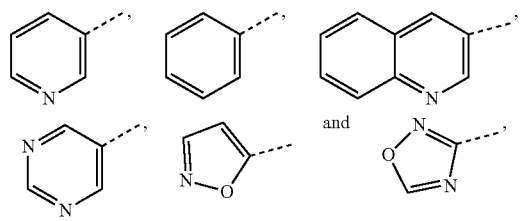

each of which is optionally substituted with 1, 2 or 3 R, but $R_3$ is not phenyl and other variables are as defined in the present invention.

In some embodiments of the present invention, $R_3$ is

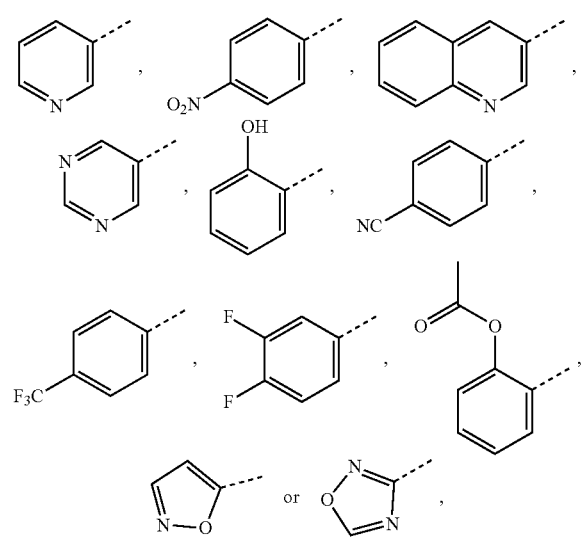

and other variables are as defined in the present invention.

In some embodiments of the present invention, $R_4$ is H, F, Cl, Br, I, OH, $NH_2$, $CH_3$ or $-CH_2-CH_3$, and other variables are as defined in the present invention.

In some embodiments of the present invention, $R_5$ is H or $CH_3$, and other variables are as defined in the present invention.

In some embodiments of the present invention, $R_6$ is H or $CH_3$, and other variables are as defined in the present invention.

In some embodiments of the present invention, $R_7$ is H, OH, COOH, $CONH_2$, $NH_2$, SH, $NH_2C(=NH)NH-$, or $R_7$ is selected from the group consisting of $C_{1-6}$ alkyl, $C_{1-3}$ alkyl-S—$C_{1-3}$ alkyl-, $C_{1-6}$ alkoxy, $C_{1-6}$ alkylthio, phenyl,

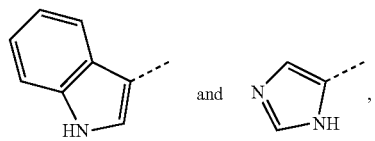

each of which is optionally substituted with 1, 2 or 3 R, and other variables are as defined in the present invention.

In some embodiments of the present invention, $R_7$ is H, OH, COOH, $CONH_2$, $NH_2$, $NH_2C(=NH)NH-$, SH, $CH_3S-$,

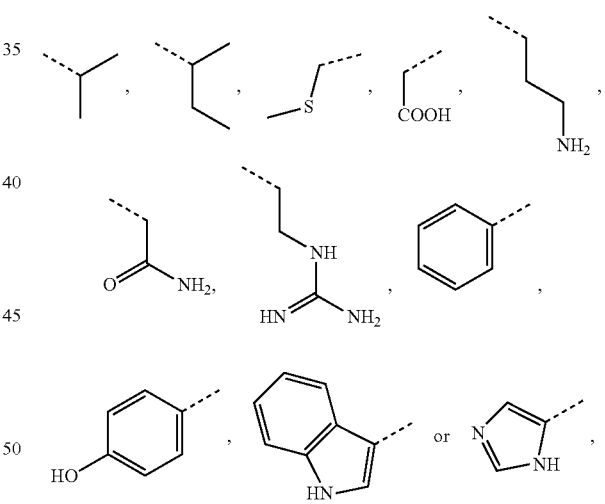

and other variables are as defined in the present invention.

In some embodiments of the present invention, $R_7$ and $R_4$ are linked together to form a 3-10-membered ring, the 3-10-membered ring is

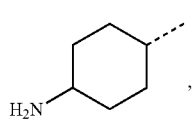

and other variables are as defined in the present invention.

In some embodiments of the present invention, $R_7$ and $R_6$ are linked together to form a 3-10-membered ring, the 3-10-membered ring is

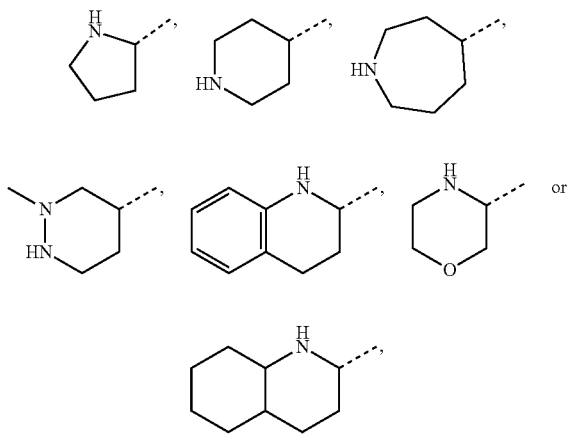

and other variables are as defined in the present invention.

In some embodiments of the present invention, $R_4$ and $R_6$ are linked to $R_7$ to form a 3-10-membered ring, the 3-10-membered ring is

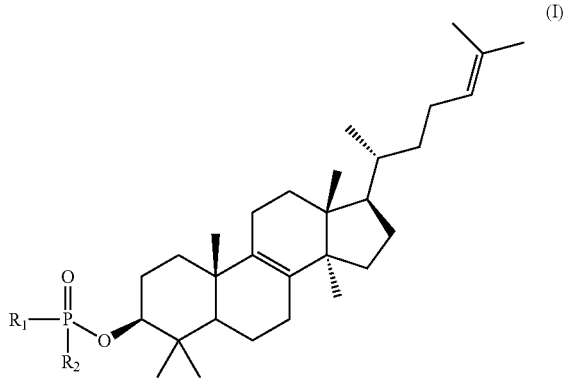

and other variables are as defined in the present invention.

In some embodiments of the present invention, $R_8$ is H or $CH_3$, and other variables are as defined in the present invention.

In some embodiments of the present invention, $R_9$ is H or $CH_3$, and other variables are as defined in the present invention.

The present invention also provides a compound represented by formula (I), (II) or (III), a pharmaceutically acceptable salt or an isomer thereof,

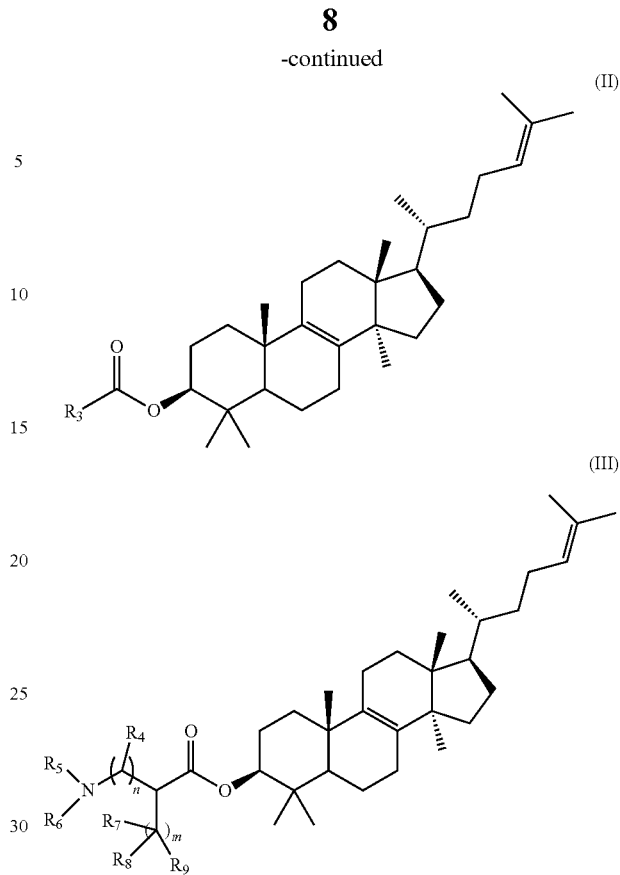

wherein, m is 0, 1, 2, 3, 4, 5 or 6, when m is 0, the moiety is absent;

n is 0, 1, 2 or 3;

$R_1$ is $C_{1-3}$ alkyl-O—C(=O)—$C_{1-3}$ alkyl-NH— which is optionally substituted with 1, 2 or 3R;

$R_2$ is selected from the group consisting of phenyl-O— and 5-10-membered heteroaryl, each of which is optionally substituted with 1, 2 or 3 R;

$R_3$ is selected from the group consisting of 6-10-membered aryl, 6-10-membered aryl-$C_{1-3}$ alkyl-, 5-10-membered heteroaryl and 5-10-membered heteroaryl-$C_{1-3}$ alkyl-, each of which is optionally substituted with 1, 2 or 3 R;

$R_4$ is H, F, Cl, Br, I, OH or $NH_2$, or $C_{1-6}$ alkyl which is optionally substituted with 1, 2 or 3 R;

$R_5$ is H, or $C_{1-6}$ alkyl which is optionally substituted with 1, 2 or 3 R;

$R_6$ is H, or $C_{1-6}$ alkyl which is optionally substituted with 1, 2 or 3 R;

$R_7$ is H, F, Cl, Br, I, OH, COOH, $CONH_2$, $NH_2$, SH or $NH_2C(=NH)NH$—, or $R_7$ is selected from the group consisting of $C_{1-6}$ alkoxy, $C_{1-6}$ alkylthio, aryl and 5-10-membered heteroaryl, each of which is optionally substituted with 1, 2 or 3 R;

or $R_7$ and $R_6$ are linked together to form a 3-10-membered ring;

or $R_7$ and $R_4$ are linked together to form a 3-10-membered ring;

or $R_4$ and $R_6$ are linked to $R_7$ to form a 3-10-membered ring;

$R_8$ is H or $C_{1-3}$ alkyl;

$R_9$ is H or $C_{1-3}$ alkyl;

R is F, Cl, Br, I, $NH_2$, $NO_2$, OH or COOH, or $C_{1-3}$ alkyl;

the "hetero" in the 5-10-membered heteroaryl or $C_{1-6}$ heteroalkyl is independently selected from the group consisting of —NH—, N, —O— and —S—;

in any of the above cases, the number of heteroatom or heteroatom group is independently 1, 2 or 3.

In some embodiments of the present invention, R is F, Cl, Br, I, $NH_2$, $NO_2$, OH, COOH, $CH_3$ or $CH_3CH_2$—.

In some embodiments of the present invention, $R_1$ is

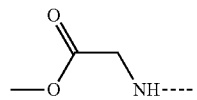

which is optionally substituted with 1, 2 or 3 R.

In some embodiments of the present invention, $R_1$ is

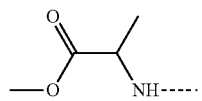

In some embodiments of the present invention, $R_2$ is

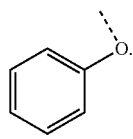

In some embodiments of the present invention, $R_3$ is selected from the group consisting of phenyl, thienyl, pyridyl and quinolyl, each of which is optionally substituted with 1, 2 or 3 R.

In some embodiments of the present invention, $R_3$ is selected from the group consisting of

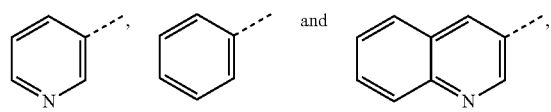

each of which is optionally substituted with 1, 2 or 3 R.

In some embodiments of the present invention, $R_3$ is

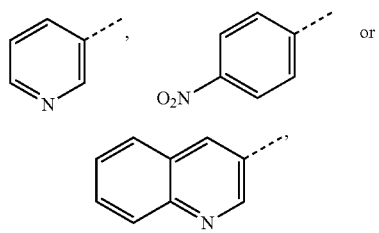

In some embodiments of the present invention, $R_7$ is H, OH, COOH, $CONH_2$, $NH_2$, SH or $NH_2C(=NH)NH$—, or $R_7$ is selected from the group consisting of $C_{1-6}$ alkoxy, $C_{1-6}$ alkylthio, phenyl,

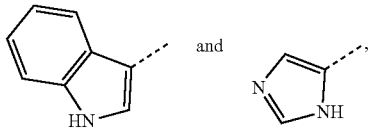

each of which is optionally substituted with 1, 2 or 3 R.

In some embodiments of the present invention, $R_7$ is H, OH, COOH, $CONH_2$, $NH_2$, $NH_2C(=NH)NH$—, SH, $CH_3S$—,

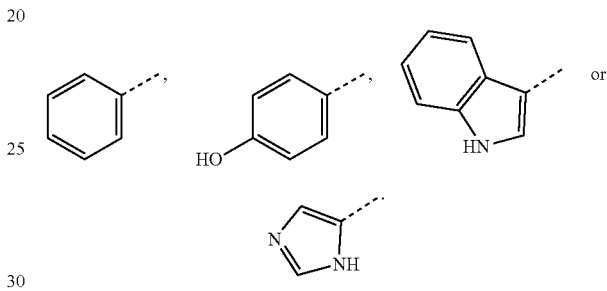

In some embodiments of the present invention, $R_7$ and $R_4$ are linked together to form a 3-10-membered ring, the 3-10-membered ring is

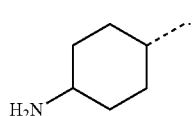

In some embodiments of the present invention, $R_7$ and $R_6$ are linked together to form a 3-10-membered ring, the 3-10-membered ring is

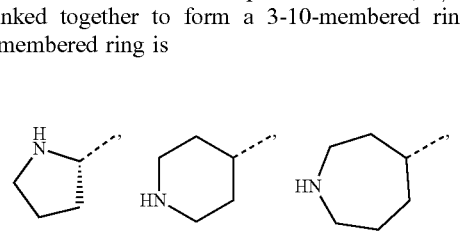

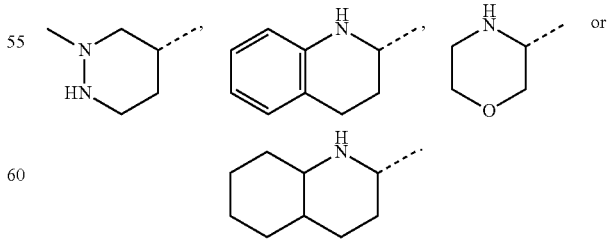

In some embodiments of the present invention, $R_4$ and $R_6$ are linked to $R_7$ to form a 3-10-membered ring, the 3-10-membered ring is

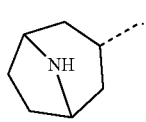
Other embodiments of the present invention can be obtained by combining the above variables arbitrarily.
This present invention also provides a compound, a pharmaceutically acceptable salt or an isomer thereof, which is selected from the group consisting of:
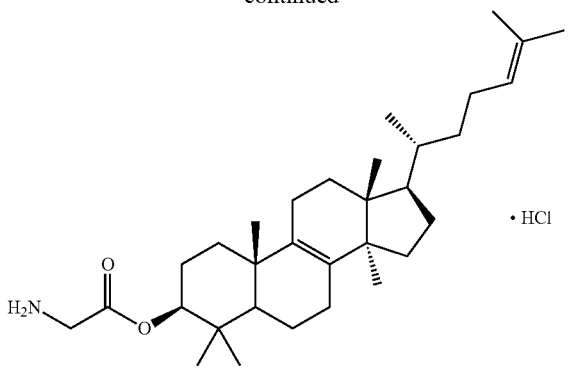
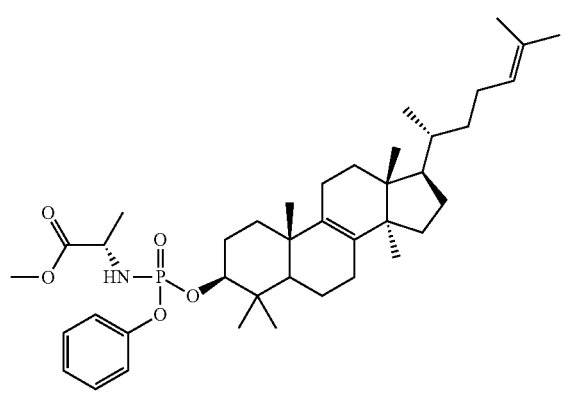
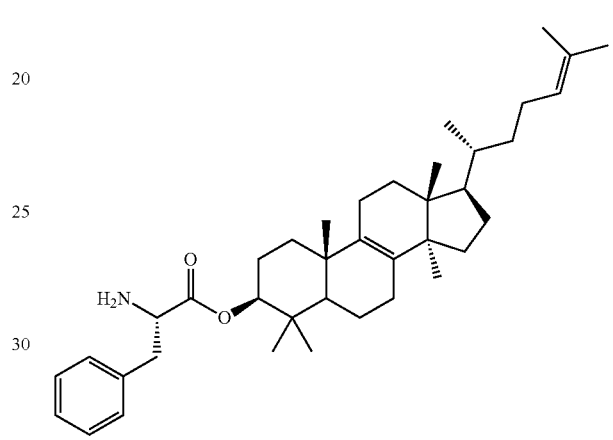
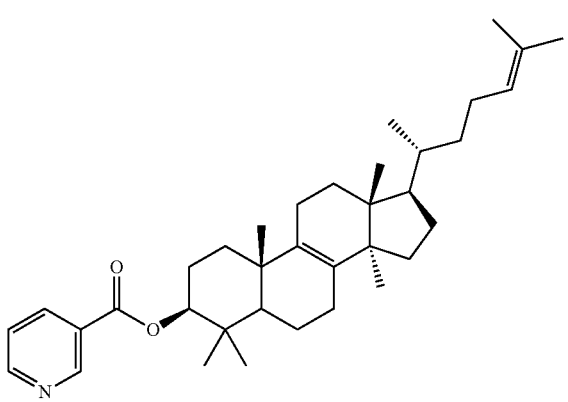
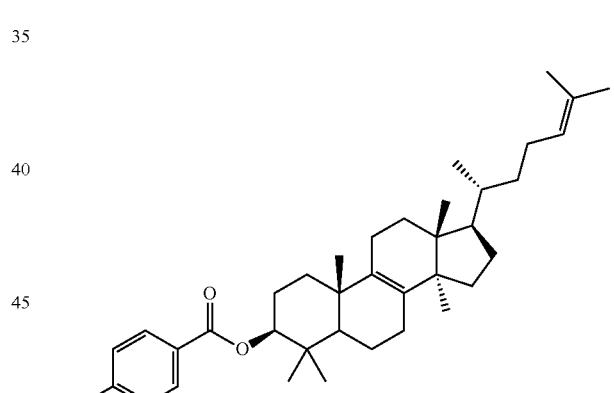
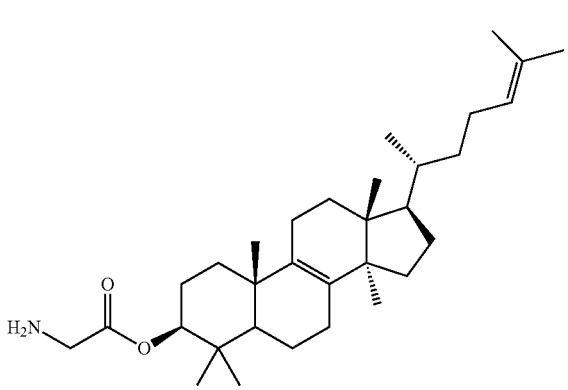
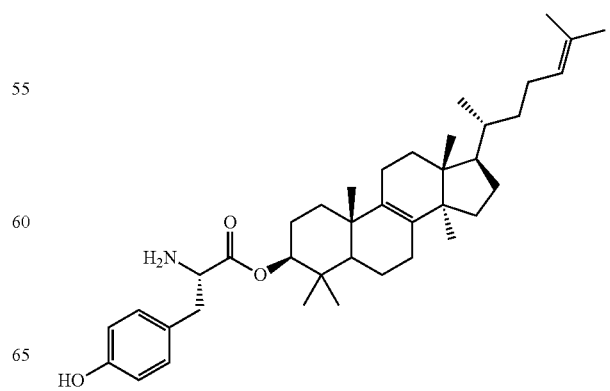

13
-continued
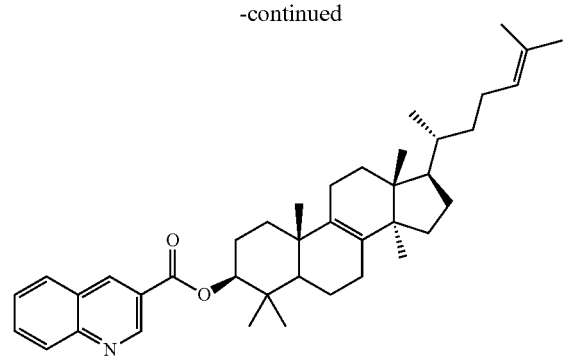
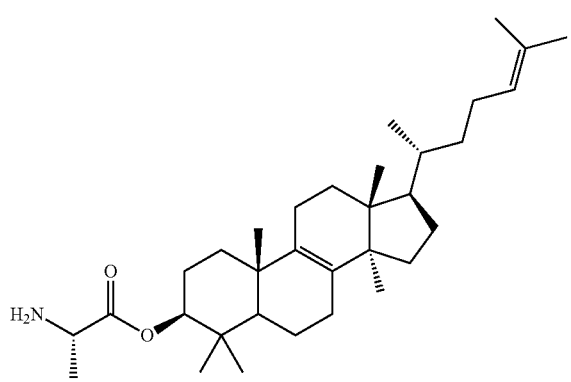
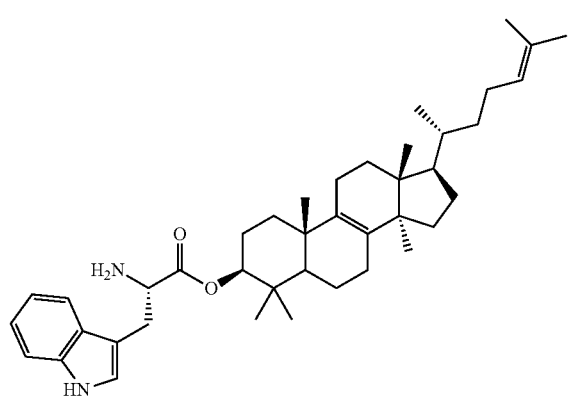
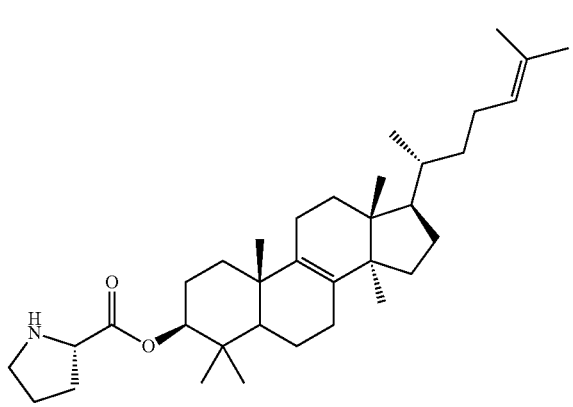
14
-continued
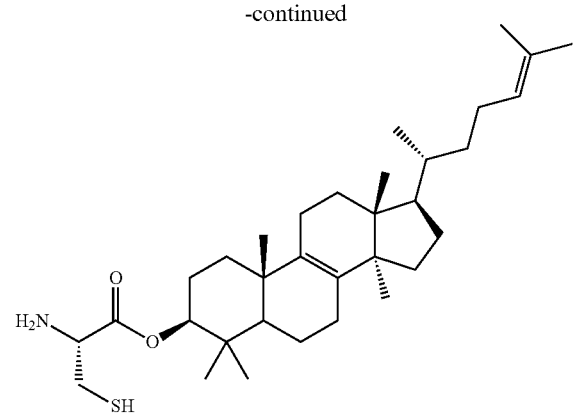
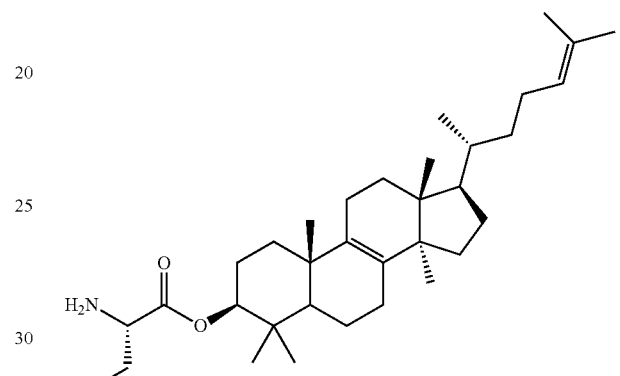
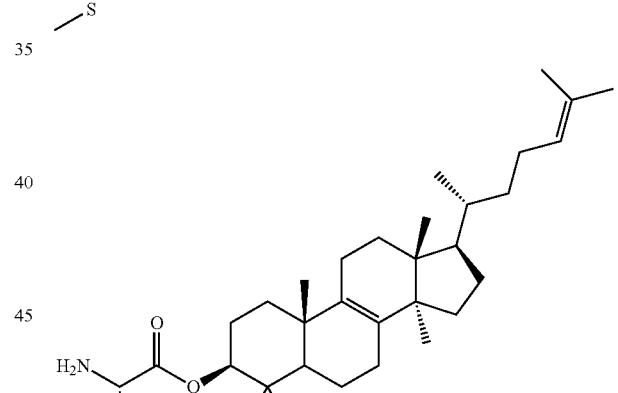
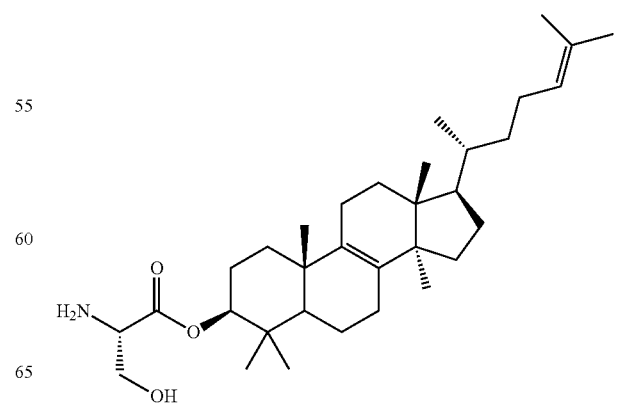

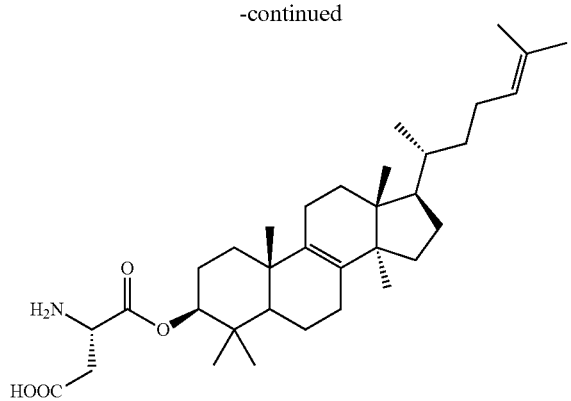
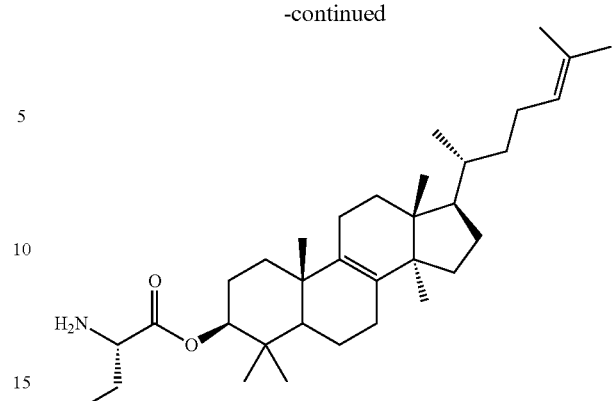
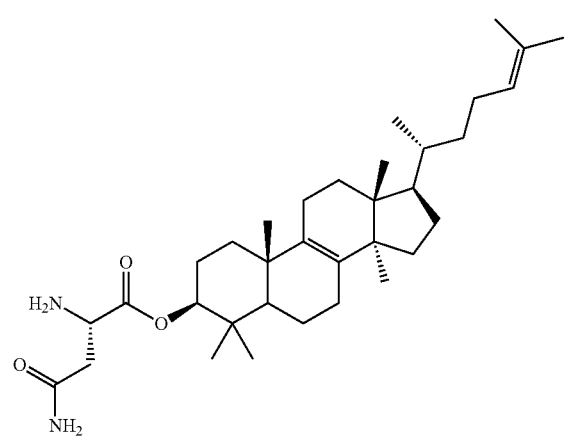
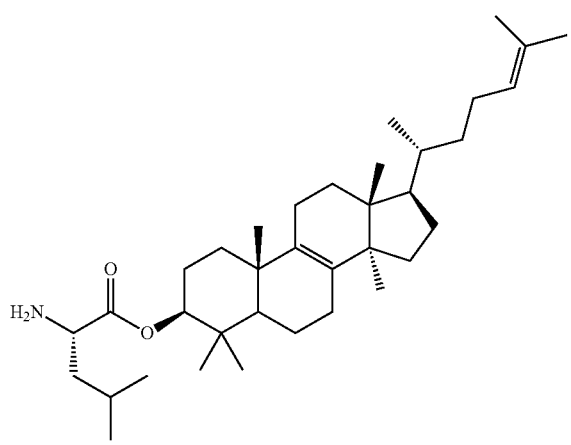
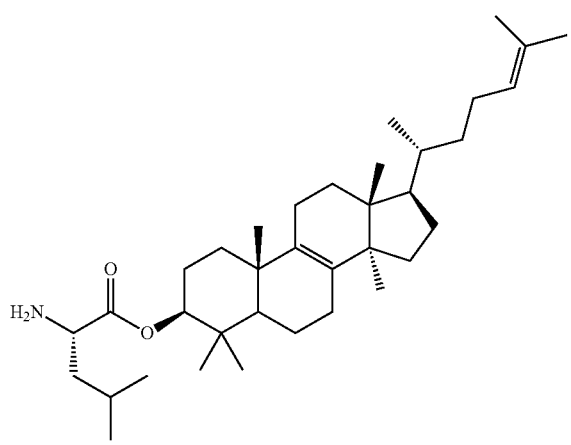

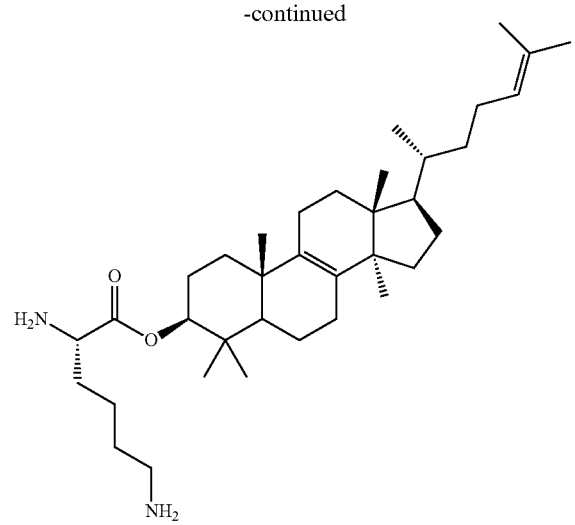
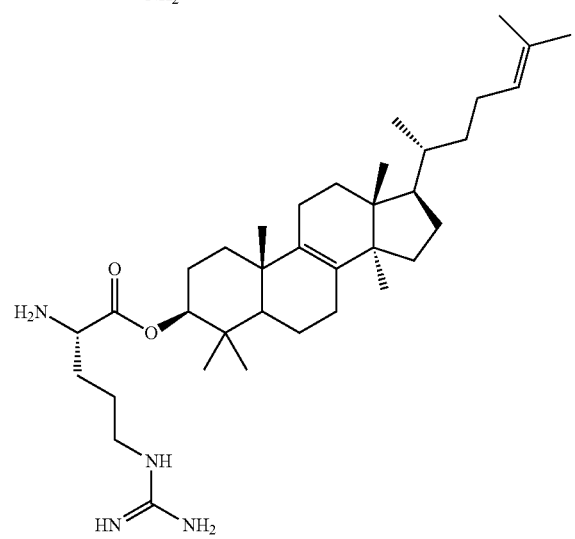
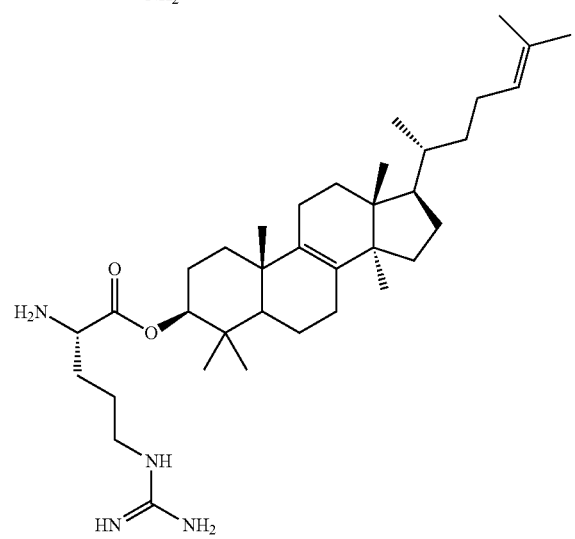
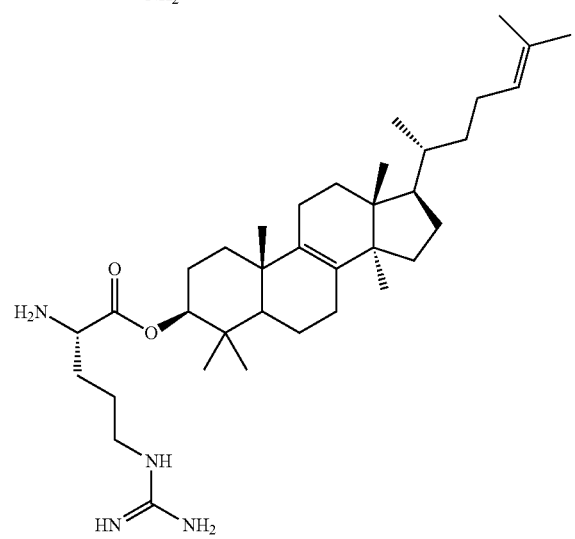
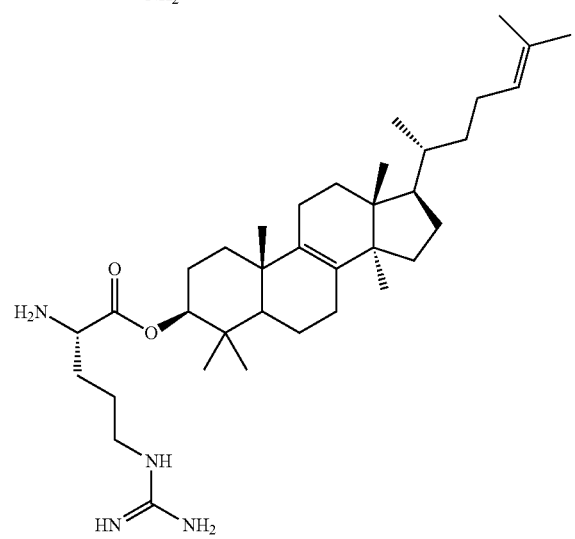
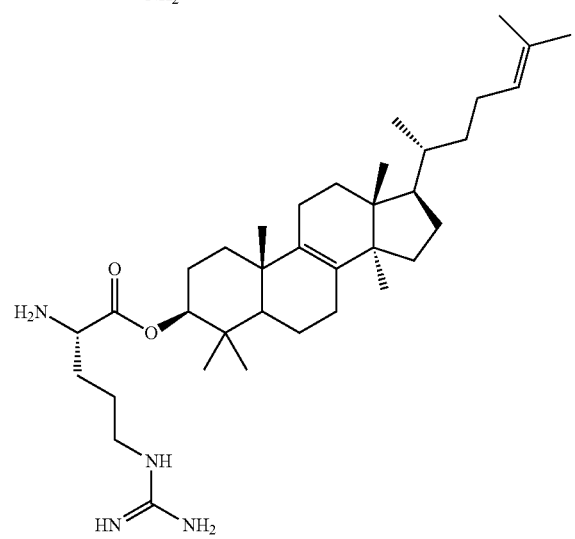
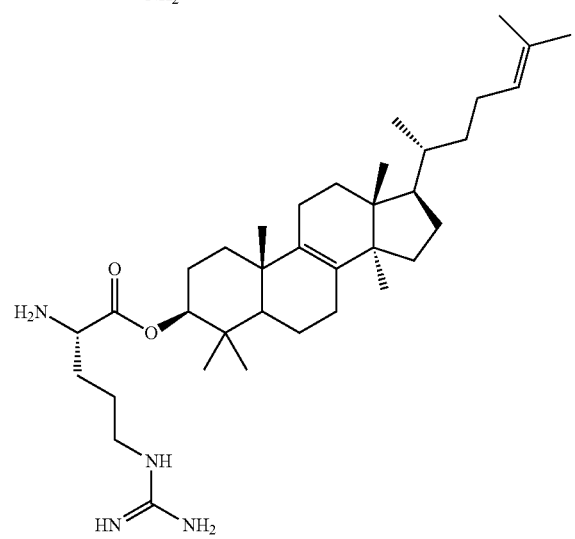
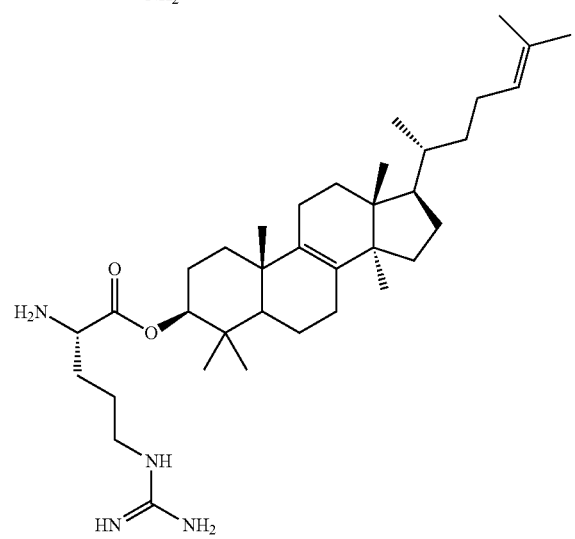
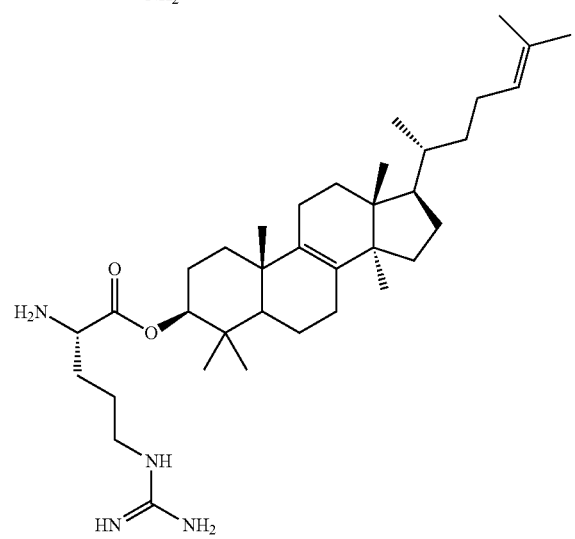
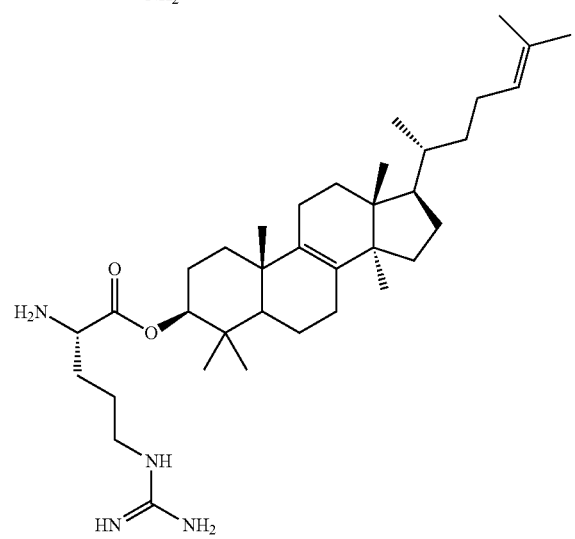
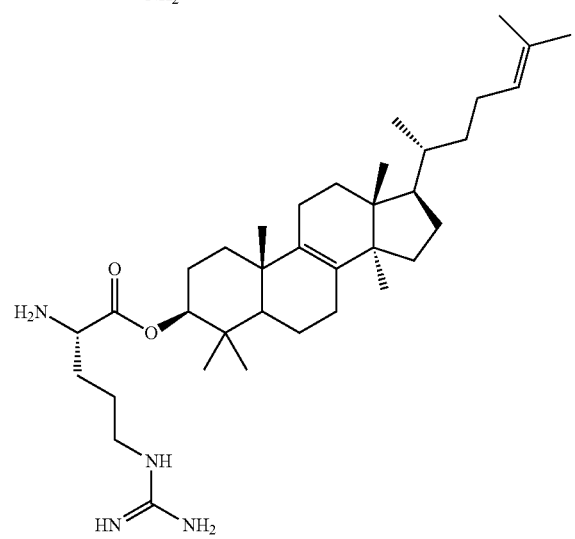

19
-continued
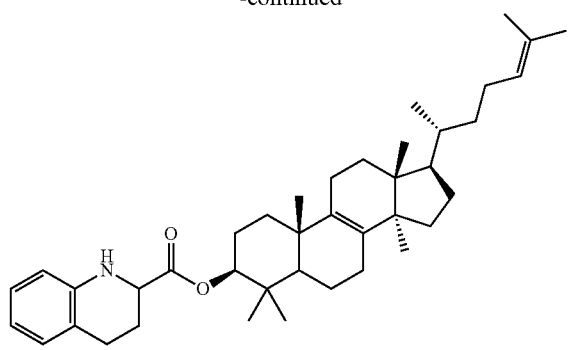
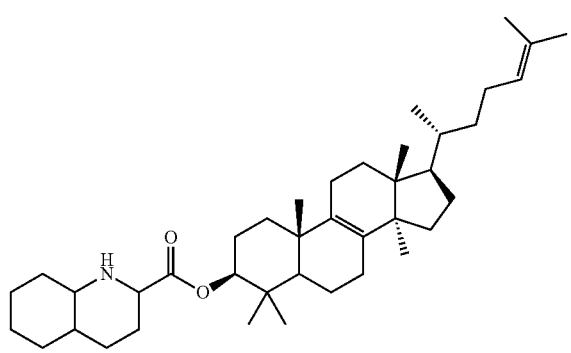
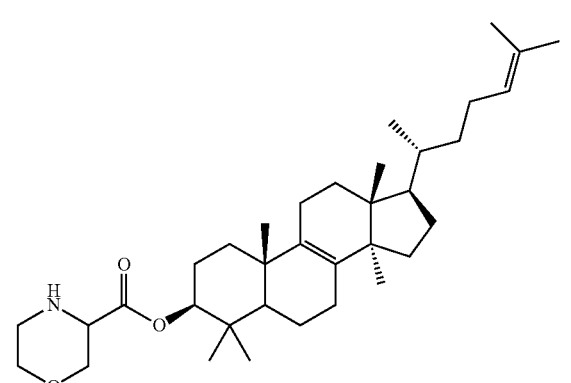
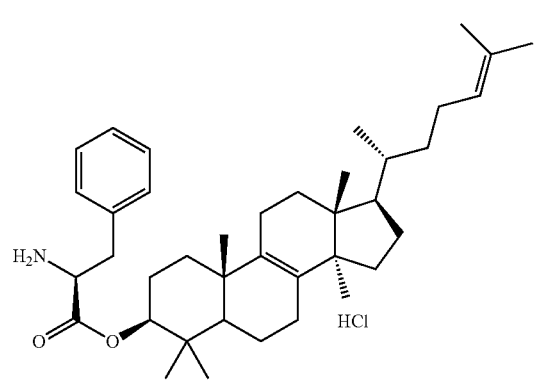
20
-continued
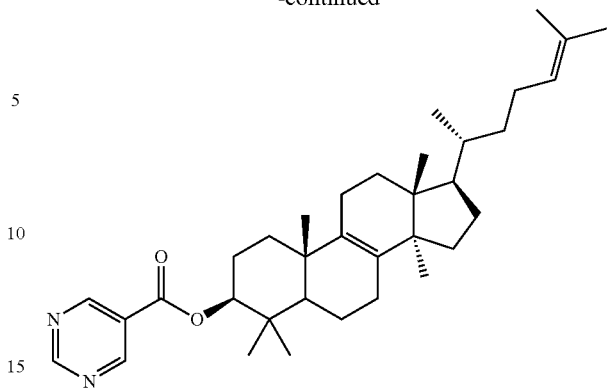
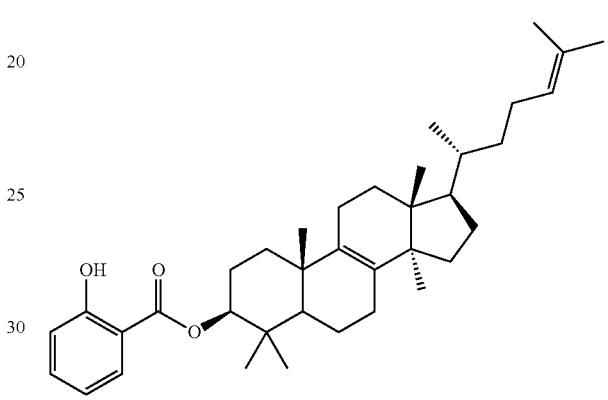
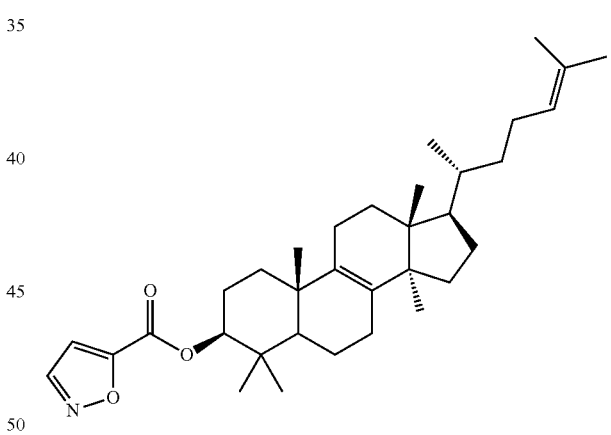
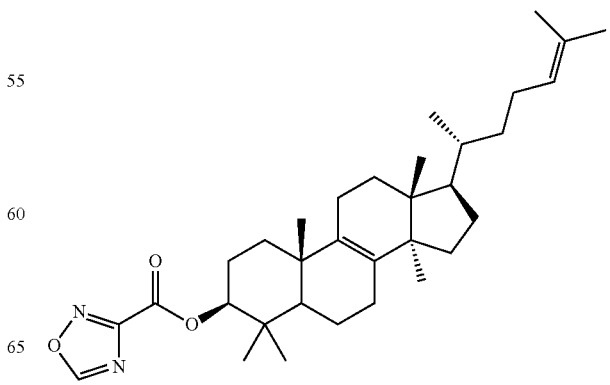

21
-continued

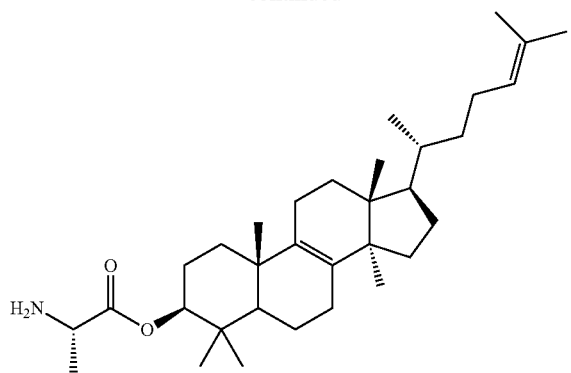

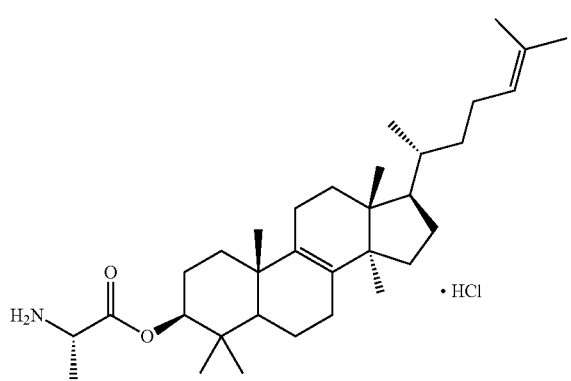
· HCl

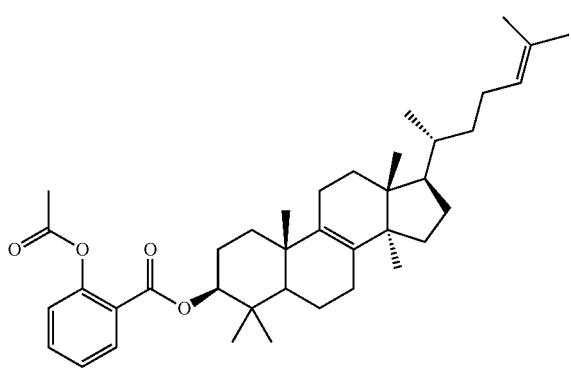

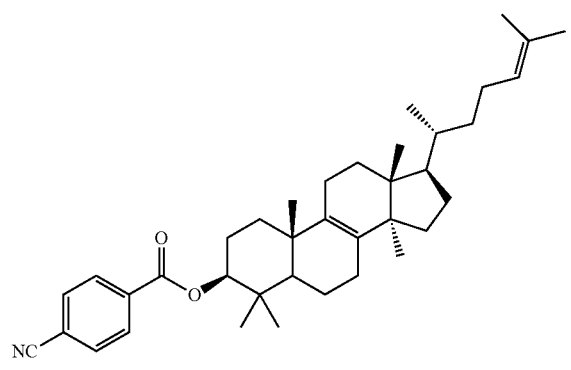

22
-continued

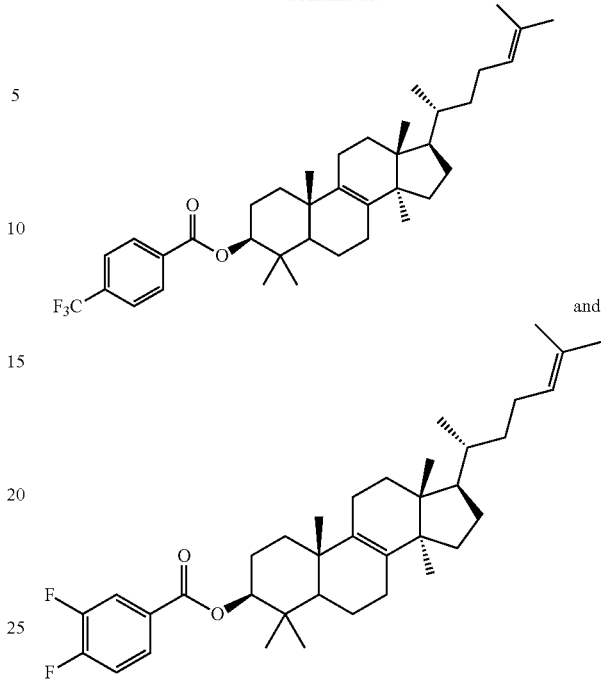
and

The present invention also provides a pharmaceutical composition comprising a therapeutically effective amount of the compound or the pharmaceutically acceptable salt thereof as active ingredient and a pharmaceutically acceptable carrier.

The present invention also provides a use of the compound or the pharmaceutically acceptable salt, or the pharmaceutical composition in manufacturing a medicament for treating ophthalmic diseases.

In some embodiments of the present invention, the medicament for treating ophthalmic diseases is a medicament for treating cataract.

In some embodiments of the present invention, the medicament for treating cataract is eye drops.

TECHNICAL FIELD

As a novel prodrug of lanosterol, the compound of the present invention has good permeability and can be efficiently converted into lanosterol in vivo, which greatly improves the drug utilization rate of lanosterol.

Definitions and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present invention that contain both basic and acidic functional groups can be converted to any base or acid addition salt.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including hydrated form. Generally, the solvated form is equivalent to the unsolvated form, and both are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Unless otherwise indicated, the term "enantiomer" or "optical isomer" refers to stereoisomers that are mirror images of each other.

Unless otherwise indicated, the term "cis-trans isomer" or "geometric isomer" is caused by the inability of a double bond or a single bond of carbon atoms on the ring to freely rotate.

Unless otherwise indicated, the term "diastereomer" refers to stereoisomers in which the molecules have two or more chiral centers and are not mirror images of each other.

Unless otherwise indicated, "(D)" or "(+)" stands for dextrorotation, "(L)" or "(−)" stands for levorotation, "(DL)" or "(±)" stands for racemization.

Unless otherwise indicated the absolute configuration of a stereogenic center is represented by a wedged solid bond ( ) and a wedged dashed bond ( ), and the relative configuration of a stereogenic center is represented by a straight solid bond ( ) an n a straight dashed bond ( ), a wavy line ( ) represents a wedged solid bond ( ) or a wedged dashed bond ( ), or a wavy line ( ) represents a straight solid bond ( ) and a straight dashed bond ( ).

The compounds of the invention may be present in particular. Unless otherwise indicated, the terms "tautomer" or "tautomeric form" mean that the different functional isomers are in dynamic equilibrium at room temperature and can be rapidly converted into each other. If tautomers are possible (as in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some keyed electrons. A specific example of keto-enol tautomerization is the interconversion between two tautomers of pentane-2,4-dione and 4-hydroxypent-3-en-2-one.

Unless otherwise indicated, the terms "enriched in one isomer", "isomer enriched", "enriched in one enantiomer" or "enantiomeric enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the terms "excess of isomer" or "excess of enantiomer" refers to the difference between the relative percentages of the two axially chiral isomers. For example, wherein, the content of one of the isomer or enantiomer is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through conventional methods in the art to give the pure enantiomer. In addition, the enantiomer and the diastereoisomer are generally isolated through chromatography which uses a chiral stationary phase and optionally combines with a chemical derivative method (for example, carbamate generated from amine). The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability. enhance the efficacy and prolong the biological half-life of the drug. All isotopic variations of the compound of the present invention, whether radioactive or not, are encompassed within the scope of the present invention. The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is a oxygen (i.e. =O), it means two hydrogen atoms are substituted. Positions on an aromatic ring can not be substituted with a oxygen. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is selected from a single bond, it means that the two groups linked by the single bond are connected directly. For example, when L in A-L-Z represents a single bond, the structure of A-L-Z is actually A-Z.

When a substituent is absent, it means that the substituent does not exist. For example, when X is vacant in A-X, the structure of A-X is actually A. When a substituent can be linked to more than one atoms on a ring, such substituent can be bonded to any atom of the ring. For example, the structural unit

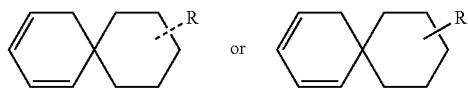

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

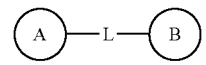

is -MW-, then -MW- can link ring A and ring B to form

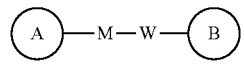

in the direction same as left-to-right reading order, and form

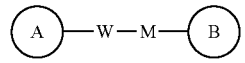

in the direction contrary to left-to-right reading order. A combination of the linking group, substituent and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. Bridged ring is also included in the definition of the heterocycle. A bridged ring is formed when one or more than one atom (i.e, C, O, N or S) link two non-adjacent carbon or nitrogen atoms. The preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, dihydrobenzofuran, chromenyl, cinnolinyl, decahydroquinolinyl, 2H,6H-1,5-2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indoliziny, indolyl, 3H-indolyl, isobenzofuranyl, isoindolinyl, isoindolyl, isoquinolinyl, isothiazolyl, isoxazolyl, methylenedioxyphenyl, morpholiny, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzodiazepinyl, phenoloxazinyl phthalazinyl, piperazinyl, piperidinyl, piperidonyl, 4-piperidonyl, piperonyl, pteridinyl, purinyl, pyranyl, pyrazinyl, pyrazolidinyl, pyrodazinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroidoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolyl, thiophenyl, thienooxazolyl, thienothiazolyl, thienoimidazole, thienyl, triazinyl, 1H-1,2,3-triazolyl, 2H-1,2,3-triazolyl, 1H-1,2,4-triazolyl, 4H-1,2,4-triazolyl, and xanthenyl. Also included are fused ring and spiro compounds.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon group or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched atomic group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homologs or isomers of n-amyl, n-hexyl, n-heptyl, n-octyl and other atomic groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or in combination with another term, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon group or a combination thereof which has a specified number of carbon atoms and at least one heteroatom. In a specific embodiment, the heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkxoy) are used by conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, "cycloalkenylalkyl" or "cycloalkenylalkyl" refers to a alkyl substituted with cycloalkenyl.

Unless otherwise specified, "cycloalkynylalkyl" or "cycloalkynylalkyl" refers to alkyl substituted with cycloalkynyl.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is meant to include, but not limited to, trifluoromethyl, 2,2,2-trifluoroethyl, 4-chlorobutyl, 3-bromopropyl and the like. Unless otherwise specified, examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, C$_{1-6}$ alkoxy includes C$_1$, C$_2$, C$_3$, C$_4$, C$_5$ and C$_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "arylalkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxymethyl-3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "mercapto protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TB S) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The present invention employs the following abbreviations: aq represents aqueous; HATU represents O-(7-azabenzotriazol-1-yl)-N,N,N,N-tetramethyl-uroniumhexafluorophosphate; EDC represents N-(3-Dimethylaminopropyl)-N'-ethylcarbodiimide hydrochloride; m-CPBA means 3-chloroperoxybenzoic acid; eq represents equivalent or equal; CDI represents carbonyldiimidazole; DCM represents dichloromethane; PE represents petroleum ether; DIAD means diisopropyl azodiformate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butylcarbonyl, which is an amine protecting group; HOAc represents acetic acid; NaCNBH3 represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents ethyldiisopropylamine; SOCl$_2$ represents thionyl chloride; CS$_2$ represents carbon disulfide; TsOH represents p-toluenesulfonic acid; NFSI represents N-fluorobenzenesulfonimide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; lanosterol prodrug 026 represents compound 8 of the present invention, i.e., embodiment 8.

Compounds are named manually or by ChemDraw® software, the commercially available compounds use their vendor directory names.

DETAILED DESCRIPTION OF THE PREFERRED EMBODIMENT

Figure 1:
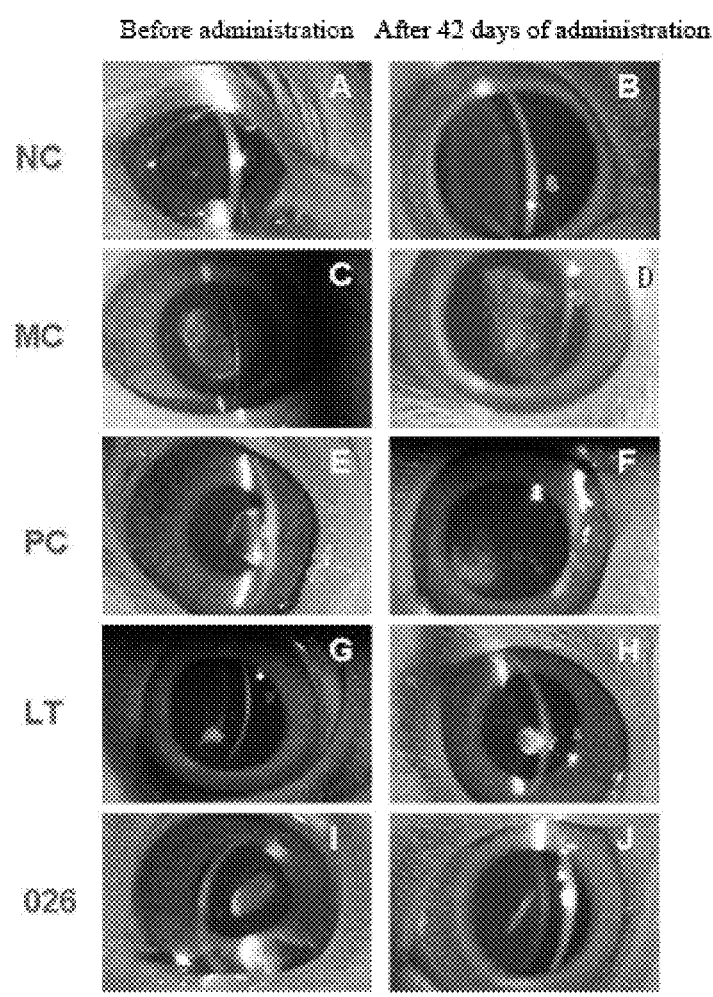
FIG. 1 is the effect of lanosterol and its prodrug 026 eye drops on sodium selenite-induced neonatal New Zealand rabbit cataract model observed by slit lamp. NC: normal control group; MC: model control group; PC: positive control group; LT: lanosterol eye drops treatment group; 026: lanosterol prodrug 026 eye drops treatment group.

The present invention will be specifically described below by way of embodiments, but the scope of the present invention is not limited thereto. While the present invention has been described in detail and with reference to specific embodiments thereof, it will be apparent to one skilled in the art that various changes and modifications can be made therein without departing from the spirit and scope thereof.

Reference Embodiment 1 Fragment BB-1

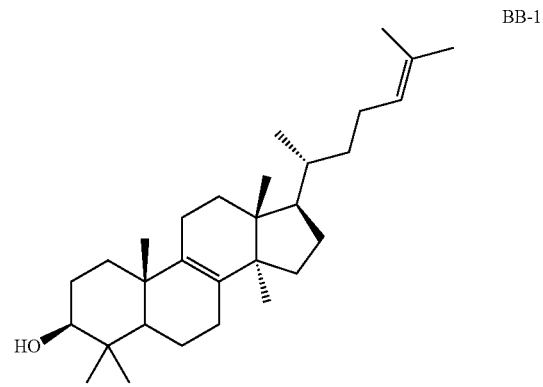 [SMILES: CC(C)=CCC[C@@H](C)[C@H]1CC[C@@]2(C)C3=C(CC[C@]12C)[C@@]1(C)CC[C@H](O)C(C)(C)C1CC3]

Synthesis Route:

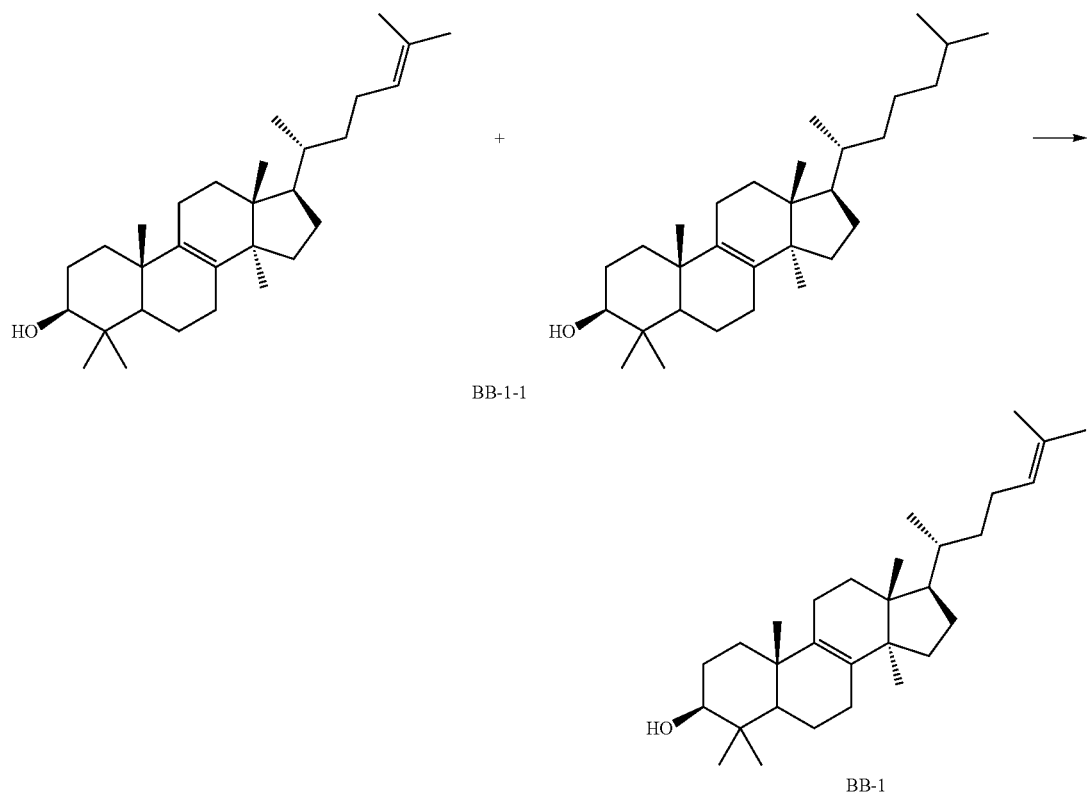

Step 1: Synthesis of Compound BB-1

The mixture BB-1-1 was separated by supercritical fluid chromatography (separation condition: column: Chiralpak AD-3 150×4.6 mm I.D., 3 μm; mobile phase: A: $CO_2$ B: ethanol (0.05% diethanolamine); gradient: B is from 5% to 40% within 5 minutes, then B is 40% for 2.5 minutes, and then B is 5% for 2.5 minutes; flow rate: 25 mL/min; column temperature: 35° C.; wavelength: 220 nm) to give compound BB-1. $^1$H NMR $^1$H NMR (CHLOROFORM-d, 400 MHz): δ=5.06-5.15 (m, 1H), 5.10 (br t, J=7.2 Hz, 1H), 3.20-3.22 (m, 1H), 3.24 (dd, J=11.5, 4.5 Hz, 1H), 1.64-2.09 (m, 15H), 0.77-1.57 (m, 29H), 0.65-0.72 ppm (m, 3H).

Embodiment 1

Synthesis Route:

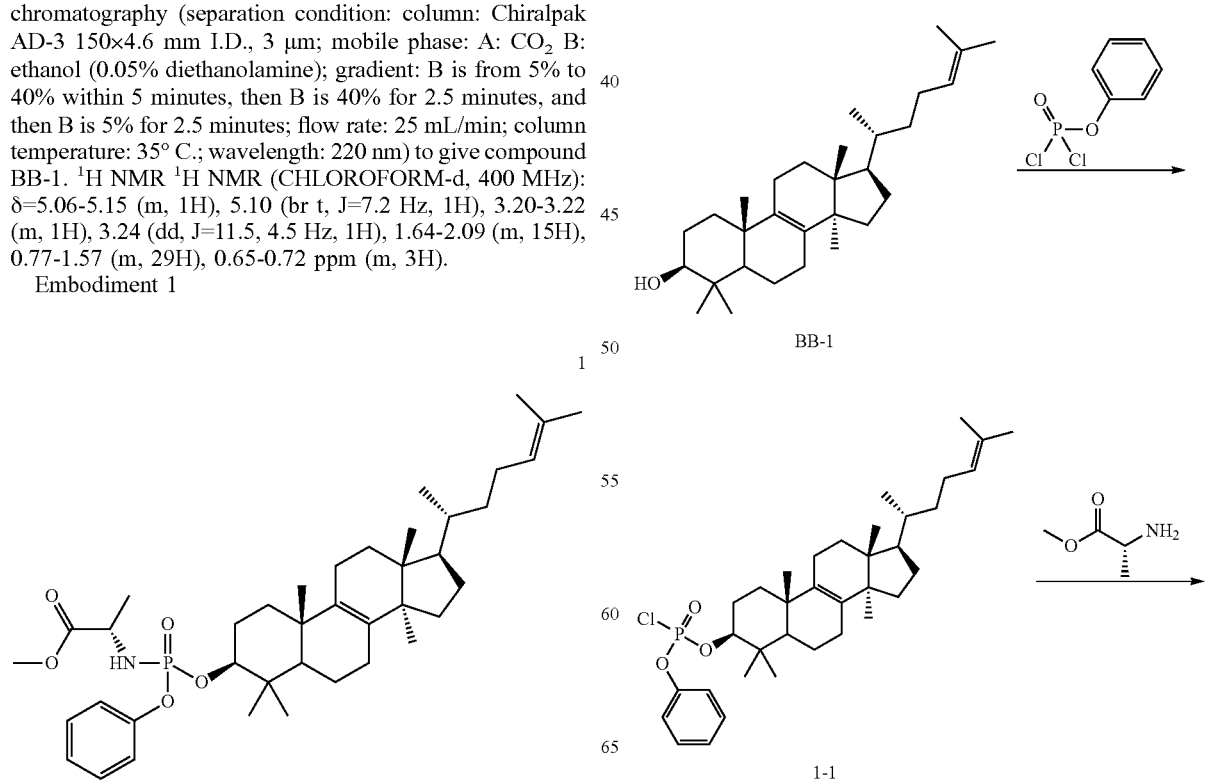

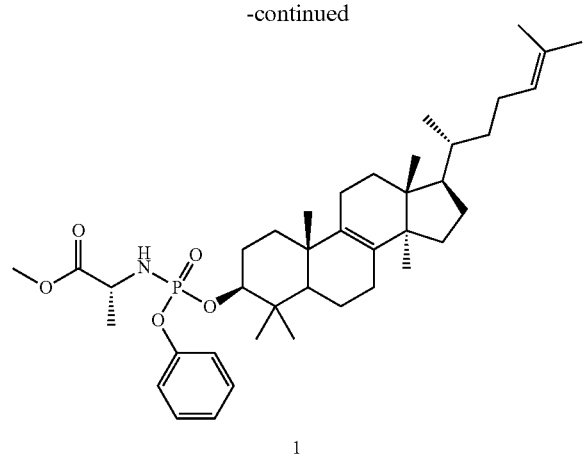

1

Step 1: Synthesis of Compound 1-1

Compound BB-1 (1.00 g, 2.34 mmol) was dissolved in dichloromethane (10 mL), and the mixture was cooled to 0° C., followed by addition of phenyl dichlorophosphate (1.48 g, 7.02 mmol) and 4-dimethylaminopyridine (1.72 g, 14.04 mmol). The mixture was warmed to room temperature under $N_2$ and stirred overnight. After the reaction was completed, the reaction was quenched with ice water, the organic phase was separated and evaporated to dryness under reduced pressure, and the residue was purified by column chromatography eluted with EA/PE (0-5%) to give targeted compound 1-1. $^1$H NMR (400 MHz, CHLOROFORM-d) δ=7.46-7.31 (m, 2H), 7.29-7.27 (m, 1H), 7.27-7.19 (m, 2H), 5.10 (br t, J=7.0 Hz, 1H), 4.52-4.20 (m, 1H), 2.15-1.96 (m, 6H), 1.92-1.66 (m, 9H), 1.56-1.46 (m, 2H), 1.43 (s, 2H), 1.38-1.11 (m, 7H), 1.08-0.99 (m, 7H), 0.93-0.85 (m, 11H), 0.68 (s, 3H).

Step 2: Synthesis of Compound 1

Compound 1-1 (500 mg, 0.8316 mmol) was dissolved in dichloromethane (10 mL), and the mixture was cooled to 0° C., followed by addition of L-alanine methyl ester hydrochloride (348.23 mg, 2.49 mmol) and 4-dimethylaminopyridine (609.59 mg, 4.99 mmol). The mixture was warmed to room temperature and stirred overnight. After the reaction was completed, the mixture was concentrated to remove solvent, and the residue was purified by column chromatography eluted with EA/PE (0-5%) to give targeted compound 1. $^1$H NMR (400 MHz, DMSO-$d_6$) δ: 2.89-2.88 (m, 2H), 2.64-2.63 (m, 2H), 2.06-2.03 (m, 1H), 1.73-1.62 (m, 4H), 1.07-1.02 (m, 2H), 0.66-0.63 (m, 2H). $^1$H NMR (400 MHz, CHLOROFORM-d) δ=7.33-7.27 (m, 2H), 7.24-7.18 (m, 2H), 7.17-7.08 (m, 1H), 5.09 (br s, 1H), 4.19-3.93 (m, 2H), 3.77-3.64 (m, 3H), 3.52-3.36 (m, 1H), 2.02 (br d, J=9.5 Hz, 6H), 1.92-1.75 (m, 3H), 1.68 (s, 4H), 1.60 (s, 3H), 1.38 (br d, J=7.0 Hz, 4H), 1.42-1.35 (m, 1H), 1.33-1.08 (m, 7H), 0.99 (t, J=5.8 Hz, 4H), 1.03 (br s, 1H), 0.93-0.79 (m, 14H), 0.67 (s, 3H).

Embodiment 2

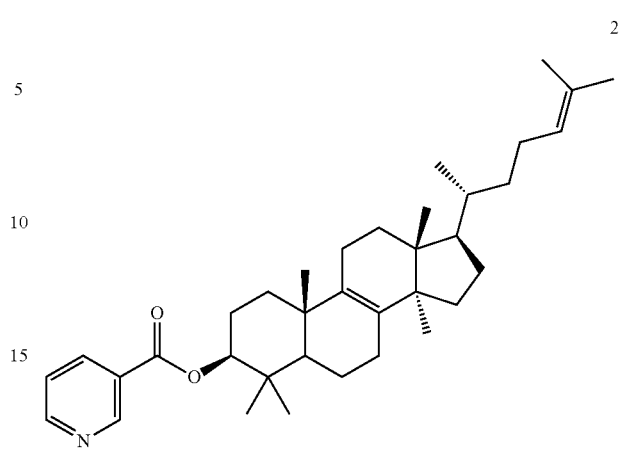

2

Synthesis Route:

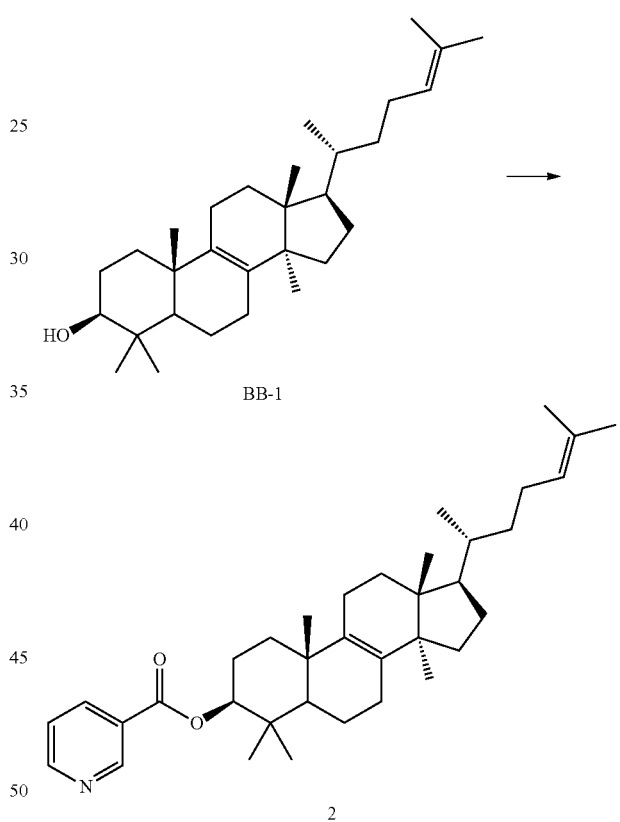

Step 1: Synthesis of Compound 2

Compound BB-1 (500 mg, 1.17 mmol) was dissolved in dichloromethane (10.00 mL), followed by addition of pyridine-3-carboxylic acid (288.08 mg, 2.34 mmol), dicyclohexylcarbodiimide (555.23 mg, 2.69 mmol) and 4-dimethylaminopyridine (328.76 mg, 2.3 mmol) under stirring at room temperature. The mixture was stirred overnight at room temperature. After the reaction was completed, the mixture was concentrated to remove solvent under reduced pressure, and the residue was purified by column chromatography eluted with EA/PE (0-5%) to give targeted compound 2. $^1$H NMR (400 MHz, CHLOROFORM-d) δ=9.24 (d, J=1.3 Hz, 1H), 8.77 (dd, J=1.8, 4.8 Hz, 1H), 8.30 (td, J=1.9, 8.0 Hz, 1H), 7.48-7.32 (m, 1H), 5.10 (br t, J=7.0 Hz, 1H), 4.85-4.73 (m, 1H), 2.10-1.67 (m, 17H), 1.56-1.16 (m, 10H), 1.05 (d, J=5.0 Hz, 7H), 0.98-0.86 (m, 10H), 0.70 (s, 3H).

Embodiment 3

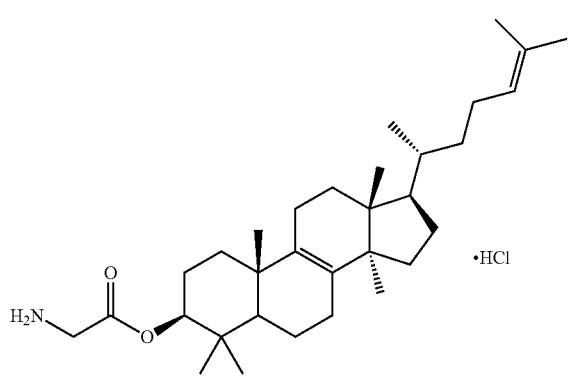

3

Synthesis Route:

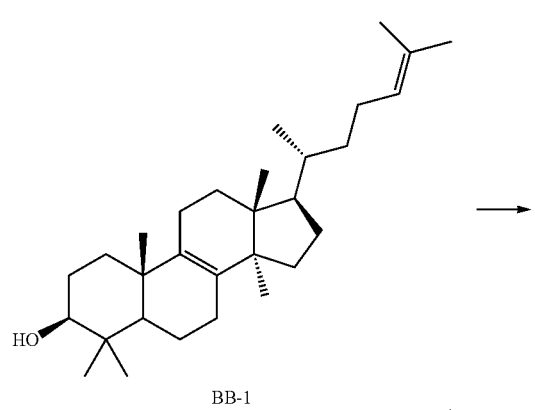

BB-1

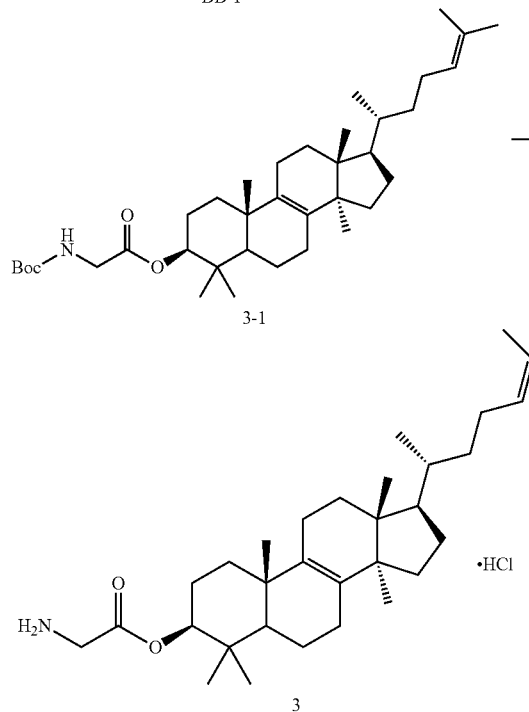

Step 1: Synthesis of Compound 3-1
Compound 3-1 was obtained according to Step 1 in embodiment 2. $^1$H NMR (400 MHz, CHLOROFORM-d) δ=5.10 (br t, J=7.0 Hz, 1H), 5.00 (br s, 1H), 4.67-4.49 (m, 1H), 3.90 (br d, J=5.3 Hz, 2H), 2.04-1.61 (m, 15H), 1.58-1.29 (m, 18H), 1.20-0.80 (m, 20H), 0.74-0.63 (m, 3H).

Step 2: Synthesis of Compound 3
Compound 3-1 (200.00 mg, 0.3425 mmol) was dissolved in dichloromethane (5.00 mL), and the mixture was cooled to 0° C., followed by slow addition of a solution of hydrogen chloride in ethyl acetate (0.5 M, 10.00 mL). The mixture was warmed to room temperature slowly and stirred overnight. After the reaction was completed, the mixture was evaporated to dryness under reduced pressure, and the targeted compound 3 was prepared with hydrochloric acid and separated. $^1$H NMR (METHANOL-$d_4$, 400 MHz): δ=5.07-5.15 (m, 1H), 4.64-4.72 (m, 1H), 3.81-3.93 (m, 2H), 1.17-2.17 (m, 30H), 0.88-1.13 (m, 14H), 0.71-0.81 ppm (m, 3H).

Embodiment 4

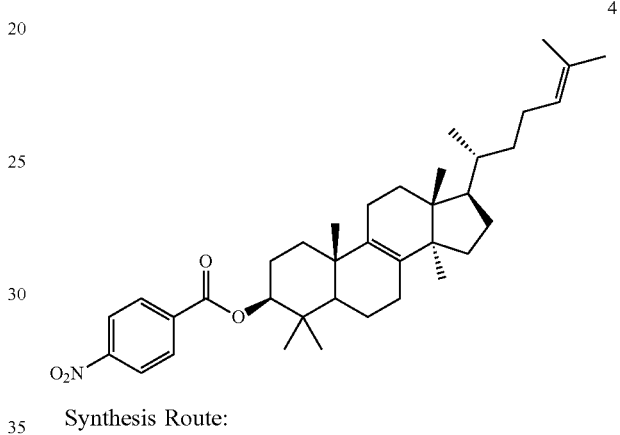

4

Synthesis Route:

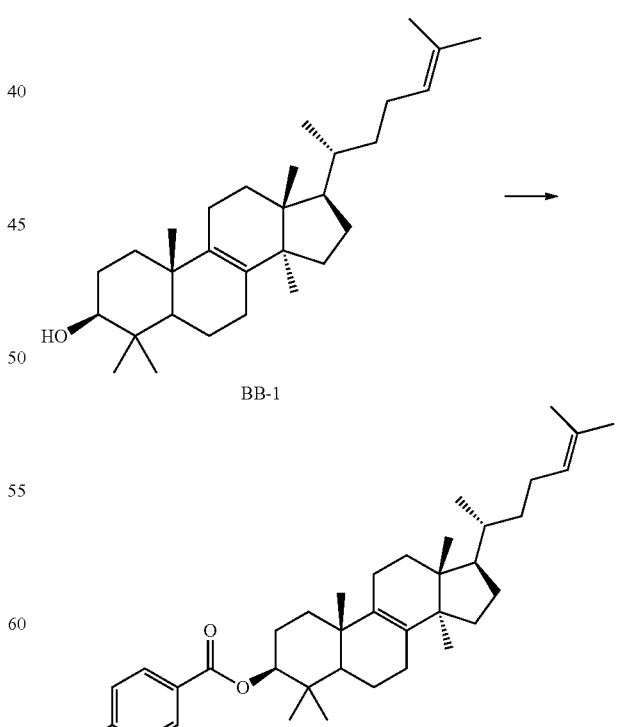

4

Step 1: Synthesis of Compound 4

Compound BB-1 (200.00 mg, 0.4687 mmol) was dissolved in dichloromethane (10.00 mL), followed by addition of 4-dimethylaminopyridine (68.71 mg, 0.5624 mmol), p-nitrobenzoic acid (93.99 mg, 0.5624 mmol) and 1-ethyl-(3-dimethylaminopropyl)carbodiimide hydrochloride (107.82 mg, 0.5624 mmol) at room temperature. The mixture was stirred at room temperature overnight. After the reaction was completed, the mixture was concentrated to remove solvent under reduced pressure, and the residue was purified by column chromatography eluted with EA/PE (0-5%) to give targeted compound 4. $^1$H NMR (CHLOROFORM-d, 400 MHz): δ=8.20-8.25 (m, 2H), 8.11-8.16 (m, 2H), 5.04 (br t, J=7.0 Hz, 1H), 4.69-4.76 (m, 1H), 1.08-2.05 (m, 29H), 0.99 (d, J=4.0 Hz, 6H), 0.89 (s, 3H), 0.85 (d, J=6.5 Hz, 3H), 0.83 (s, 3H), 0.64 ppm (s, 3H).

Embodiment 5

Step 1: Synthesis of Compound 5

Compound 5 was obtained according to step 1 in embodiment 2. $^1$H NMR (CHLOROFORM-d, 400 MHz): δ=9.41 (d, J=1.5 Hz, 1H), 8.76 (d, J=2.0 Hz, 1H), 8.10 (d, J=8.5 Hz, 1H), 7.88 (d, J=8.0 Hz, 1H), 7.77 (td, J=7.7, 1.3 Hz, 1H), 7.52-7.60 (m, 1H), 5.04 (br t, J=7.0 Hz, 1H), 4.79 (dd, J=11.3, 4.8 Hz, 1H), 1.94-2.07 (m, 5H), 1.71-1.91 (m, 6H), 1.60-1.68 (m, 6H), 1.49-1.57 (m, 5H), 1.12-1.39 (m, 7H), 1.02 (d, J=8.5 Hz, 6H), 0.93 (s, 3H), 0.80-0.87 (m, 6H), 0.64 ppm (s, 3H).

Embodiment 6

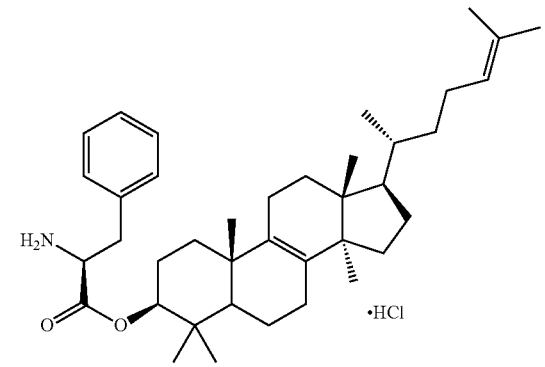

Synthesis Route:

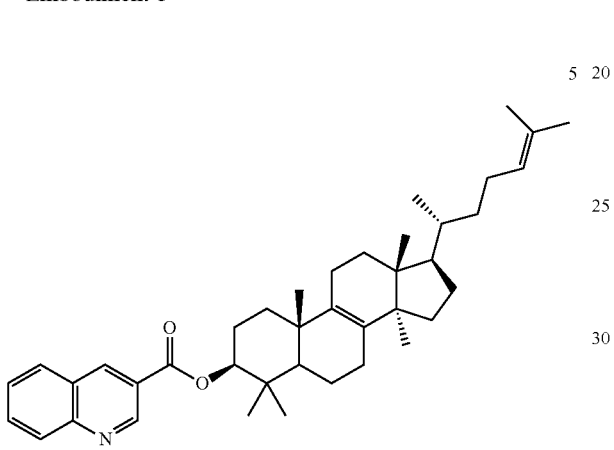

Synthesis Route:

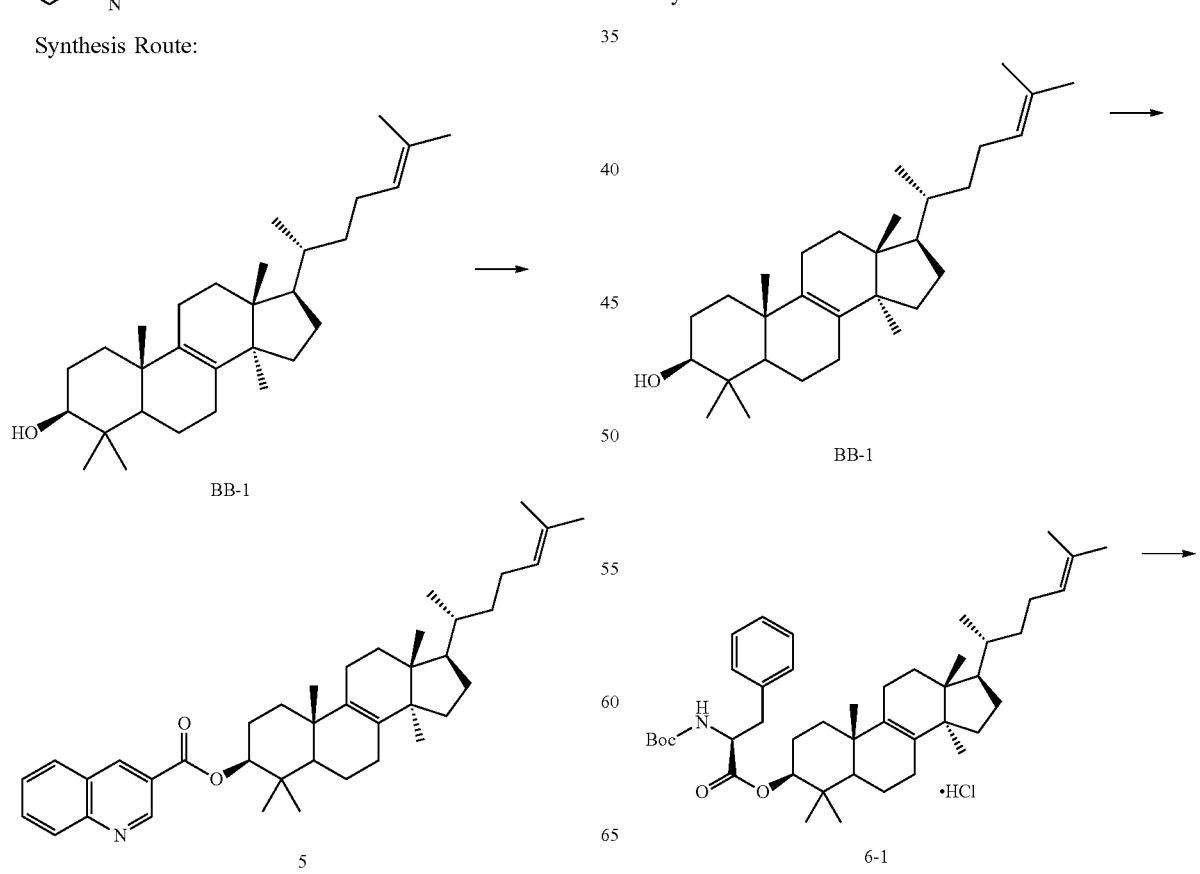

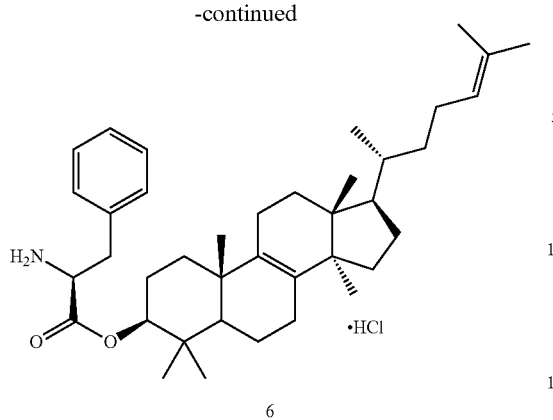

6

Step 1: Synthesis of Compound 6-1

Compound 6-1 was obtained according to step 1 in embodiment 2. $^1$H NMR (CHLOROFORM-d, 400 MHz): δ=7.19-7.25 (m, 2H), 7.14-7.18 (m, 1H), 7.08-7.13 (m, 2H), 5.03 (br t, J=7.0 Hz, 1H), 4.83 (br d, J=8.5 Hz, 1H), 4.39-4.63 (m, 2H), 2.90-3.13 (m, 2H), 1.73-2.01 (m, 8H), 1.39-1.69 (m, 16H), 1.32 (s, 9H), 1.21-1.27 (m, 2H), 0.95-1.14 (m, 3H), 0.92 (s, 3H), 0.84 (d, J=6.0 Hz, 3H), 0.80 (s, 3H), 0.75 (d, J=7.0 Hz, 6H), 0.61 ppm (s, 3H).

Step 2: Synthesis of Compound 6

Compound 6 was obtained according to step 2 in embodiment 3. $^1$H NMR (METHANOL-d$_4$, 400 MHz): δ=7.25-7.32 (m, 2H), 7.19-7.25 (m, 3H), 5.00 (br t, J=6.8 Hz, 1H), 4.50 (br dd, J=10.8, 5.3 Hz, 1H), 4.25 (br t, J=7.3 Hz, 1H), 3.19 (br s, 1H), 3.03 (dd, J=14.3, 7.8 Hz, 1H), 1.98 (br s, 5H), 1.40-1.74 (m, 15H), 1.12-1.29 (m, 7H), 0.91-0.96 (m, 3H), 0.56-0.86 ppm (m, 17H).

Embodiment 7

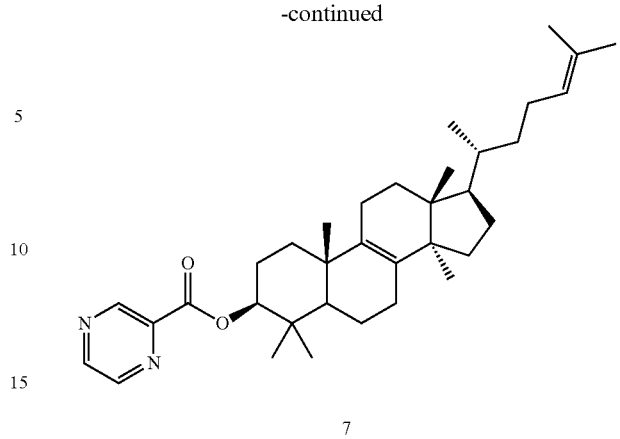

7

Step 1: Synthesis of Compound 7

Compound 7 was obtained according to step 1 in embodiment 2. $^1$H NMR (CHLOROFORM-d, 400 MHz): δ=9.30 (s, 1H), 9.22 (s, 2H), 5.03 (br t, J=7.0 Hz, 1H), 4.75 (dd, J=11.0, 4.5 Hz, 1H), 1.65-2.04 (m, 13H), 1.62 (s, 3H), 1.54 (s, 3H), 1.05-1.50 (m, 10H), 0.98 (d, J=7.5 Hz, 6H), 0.89 (s, 3H), 0.85 (br d, J=6.5 Hz, 3H), 0.80-0.83 (m, 3H), 0.63 ppm (s, 3H).

Embodiment 8

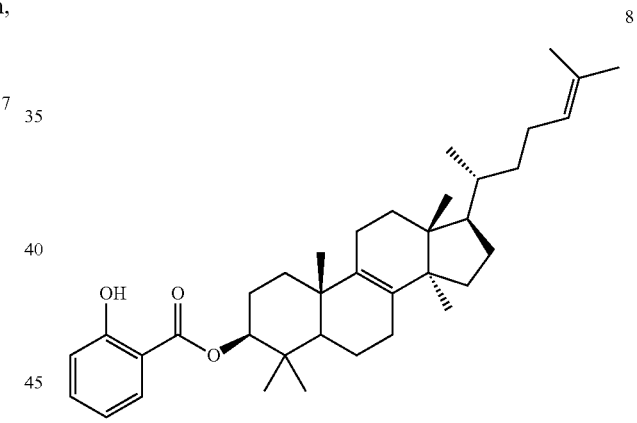

8

Synthesis Route:

Synthesis Route:

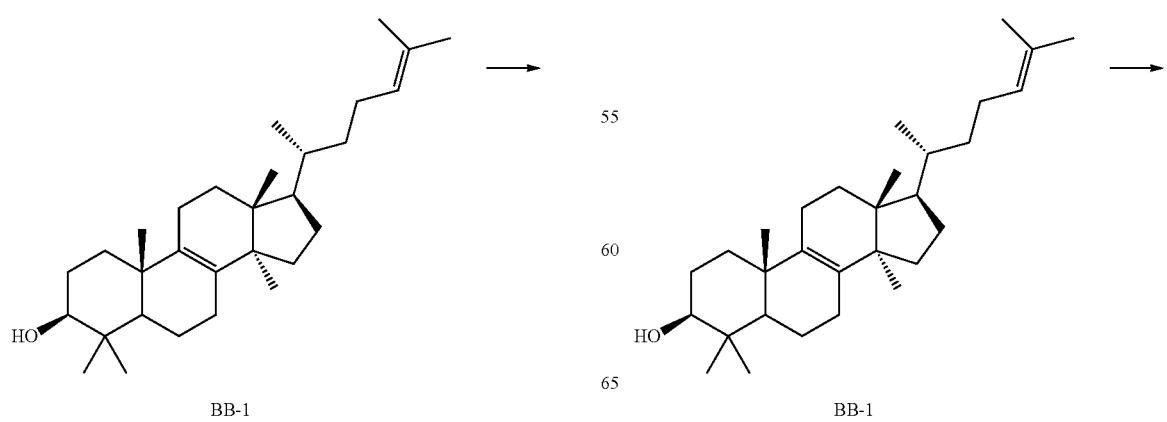

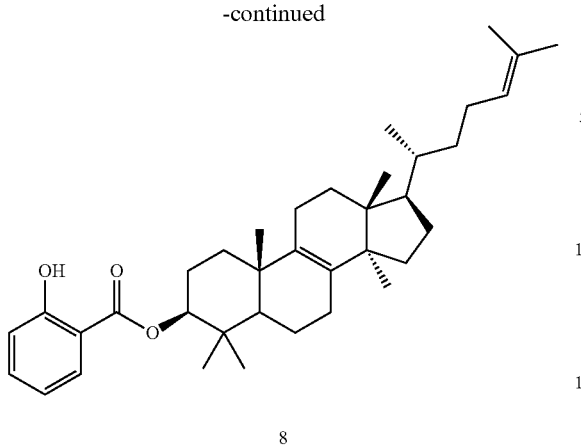

8

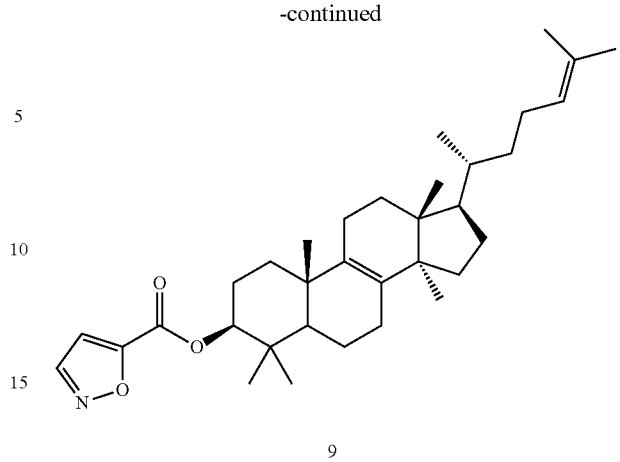

9

Step 1: Synthesis of Compound 8

Compound 8 was given according to step 1 in embodiment 2. $^1$H NMR (CHLOROFORM-d, 400 MHz): δ=10.97 (s, 1H), 7.85 (dd, J=8.0, 1.5 Hz, 1H), 7.41-7.53 (m, 1H), 6.99 (d, J=8.5 Hz, 1H), 6.89 (t, J=7.5 Hz, 1H), 5.12 (br t, J=7.0 Hz, 1H), 4.77-4.85 (m, 1H), 1.68-2.13 (m, 16H), 1.13-1.64 (m, 13H), 1.07 (d, J=3.0 Hz, 6H), 0.98 (s, 3H), 0.94 (d, J=6.5 Hz, 3H), 0.91 (s, 3H), 0.72 ppm (s, 3H).

Embodiment 9

Step 1: Synthesis of Compound 9

Compound 9 was obtained according to step 1 in embodiment 2. $^1$H NMR (400 MHz, CHLOROFORM-d) δ=8.36 (d, J=1.8 Hz, 1H), 6.93 (d, J=1.8 Hz, 1H), 5.10 (br t, J=7.2 Hz, 1H), 4.78 (dd, J=4.8, 11.0 Hz, 1H), 2.10-1.66 (m, 17H), 1.58-1.16 (m, 12H), 1.03 (d, J=14.6 Hz, 6H), 0.97-0.83 (m, 9H), 0.70 (s, 3H).

Embodiment 10

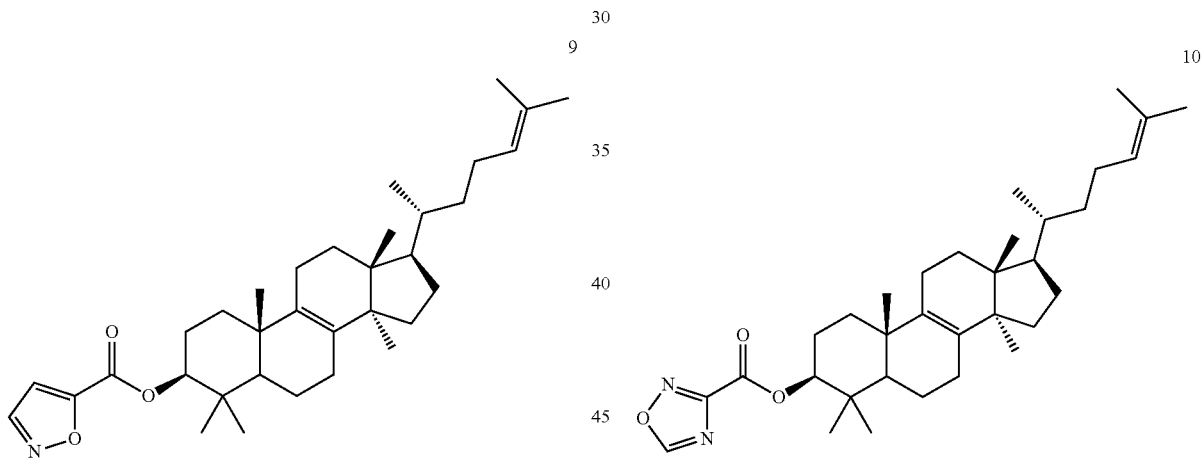

9

10

Synthesis Route:

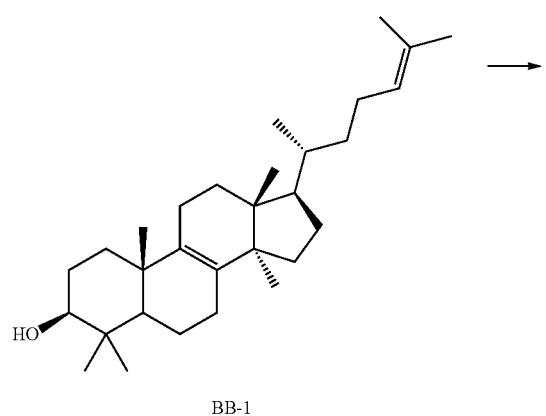

BB-1

Synthesis Route:

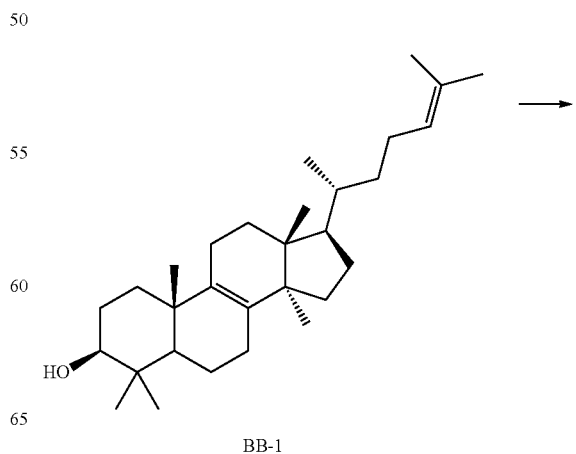

BB-1

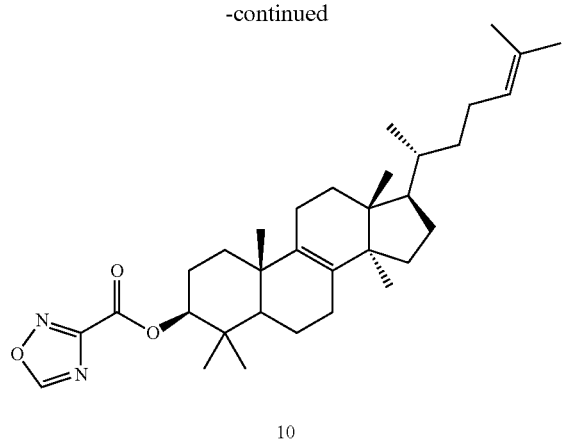

10

Step 1: Synthesis of Compound 10

Compound 10 was obtained according to step 1 in embodiment 2. ¹H NMR (400 MHz, CHLOROFORM-d) δ=8.05 (s, 1H), 5.03 (br t, J=7.0 Hz, 1H), 4.66-4.49 (m, 1H), 2.06-1.89 (m, 5H), 1.74-1.62 (m, 3H), 1.55-1.16 (m, 17H), 0.95 (s, 3H), 0.87-0.75 (m, 16H), 0.62 (s, 3H).

Embodiment 11

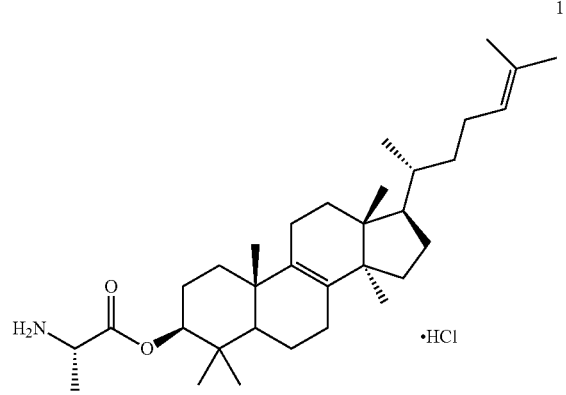

11

Synthesis Route:

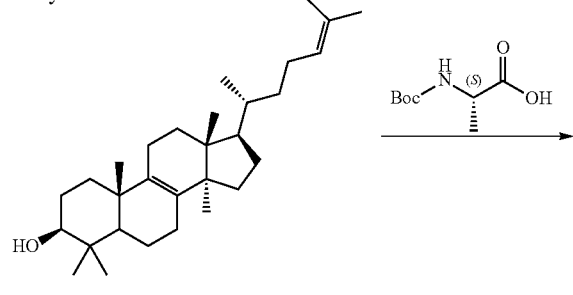

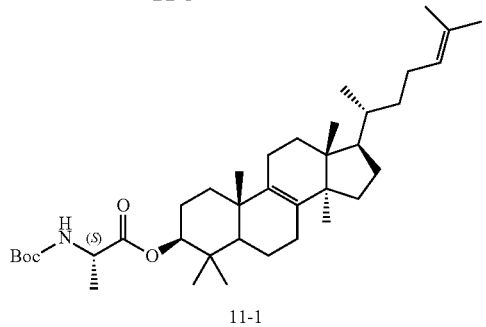

11-1

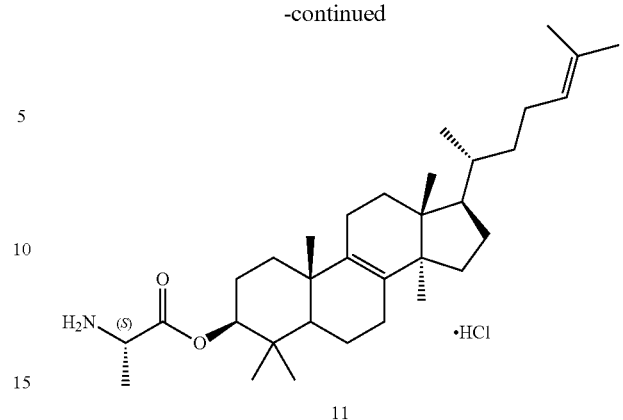

11

Step 1: Synthesis of Compound 11-1

Compound 11-1 was obtained according to step 1 in embodiment 2. ¹H NMR (400 MHz, CHLOROFORM-d) δ=5.13-4.92 (m, 2H), 4.48 (dd, J=5.0, 11.0 Hz, 1H), 4.24 (br t, J=7.0 Hz, 1H), 2.13-1.74 (m, 8H), 1.69-1.47 (m, 13H), 1.38 (s, 12H), 1.34 (br d, J=7.0 Hz, 5H), 1.20-0.72 (m, 18H), 0.62 (s, 3H).

Step 2: Synthesis of Compound 11

Compound 11 was obtained according to step 2 in embodiment 3. ¹H NMR (400 MHz, METHANOL-d₄) δ=5.12 (br t, J=7.3 Hz, 1H), 4.78-4.54 (m, 1H), 4.12 (q, J=7.0 Hz, 1H), 2.15-1.73 (m, 13H), 1.77-1.58 (m, 11H), 1.49-1.20 (m, 7H), 1.17-0.85 (m, 16H), 0.80-0.64 (m, 3H).

Embodiment 12

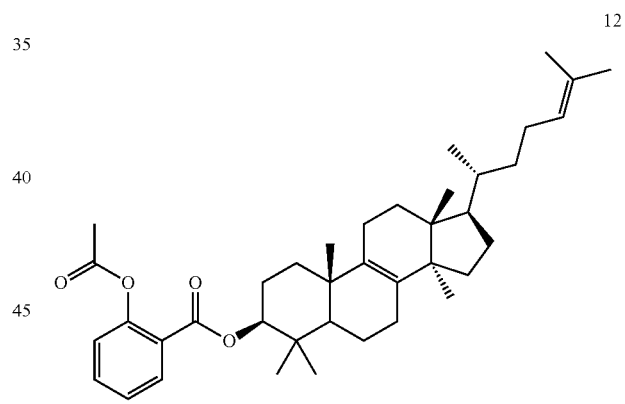

12

Synthesis Route:

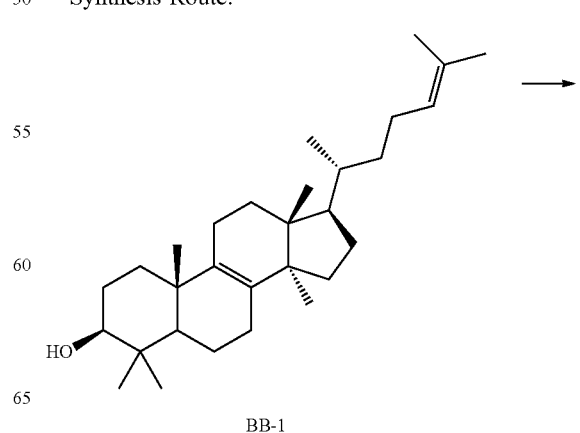

BB-1

-continued

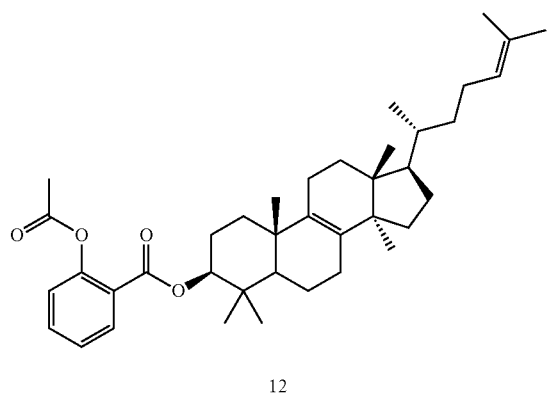

12

Step 1: Synthesis of Compound 12

Salicylic acid (632.35 mg, 3.51 mmol) was added into a reaction flask and dissolved in dichloromethane (10.00 mL), and oxalyl chloride (594.03 mg, 4.68 mmol) was added into the reaction flask dropwise. The mixture was stirred at 25° C. for 2 hours. The reaction mixture was evaporated to dryness to give a crude product. The crude product was re-dissolved in dichloromethane (20.00 mL), followed by addition of compound BB-1 (500.00 mg, 1.17 mmol) and trimethylamine (710.35 mg, 7.02 mmol). The mixture was stirred at 25° C. for 10.0 hours. The reaction mixture was diluted with water (100 mL) and extracted with dichloromethane (100 mL×2). The combined organic phase was evaporated to dryness to give a crude product, which was purified by column chromatography to give targeted compound 12. $^1$H NMR (400 MHz, CHLOROFORM-d) δ=7.96 (d, J=8.0 Hz, 1H), 7.63-7.46 (m, 1H), 7.13 (t, J=7.5 Hz, 1H), 6.98 (t, J=8.8 Hz, 1H), 5.21-4.99 (m, 1H), 3.84-3.57 (m, 1H), 2.04-1.61 (m, 17H), 1.60 (s, 3H), 1.49-1.05 (m, 11H), 1.01-0.82 (m, 13H), 0.74 (s, 3H), 0.70-0.64 (m, 3H).

Embodiment 14

14

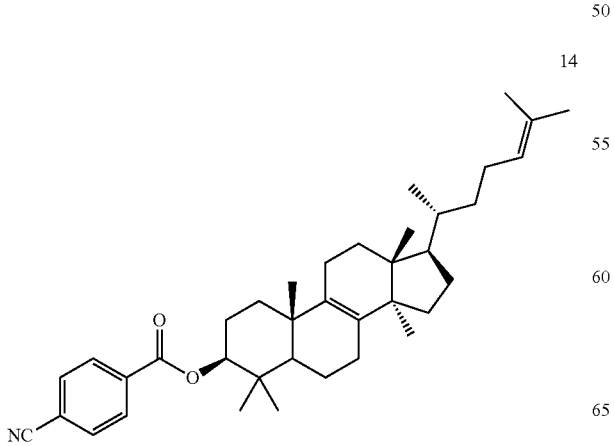

Synthesis Route:

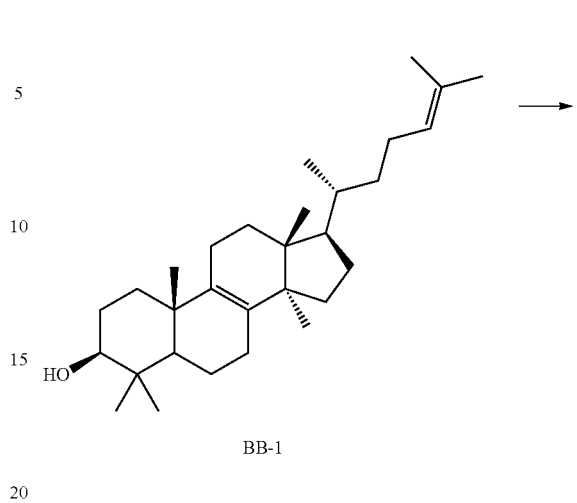

BB-1

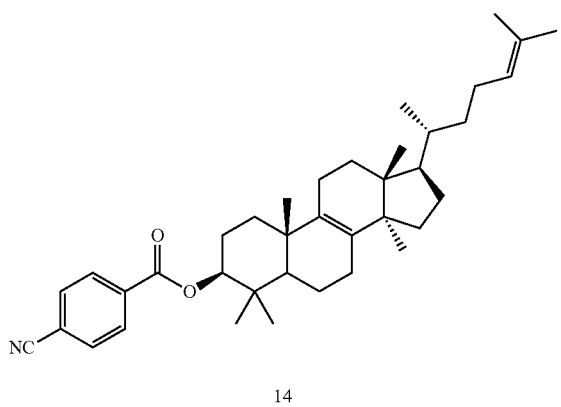

14

Step 1: Synthesis of Compound 14

Compound 14 was obtained according to step 1 in embodiment 2. $^1$H NMR (CHLOROFORM-d, 400 MHz): δ=8.06 (d, J=8.0 Hz, 2H), 7.68 (d, J=8.5 Hz, 2H), 5.04 (br t, J=7.0 Hz, 1H), 4.68-4.74 (m, 1H), 1.63-2.04 (m, 13H), 1.62 (s, 3H), 1.54 (s, 3H), 1.25-1.50 (m, 7H), 1.01-1.19 (m, 3H), 0.99 (s, 3H), 0.97 (s, 3H), 0.88 (s, 3H), 0.85 (d, J=6.0 Hz, 3H), 0.82 (s, 3H), 0.63 ppm (s, 3H).

Embodiment 15

15

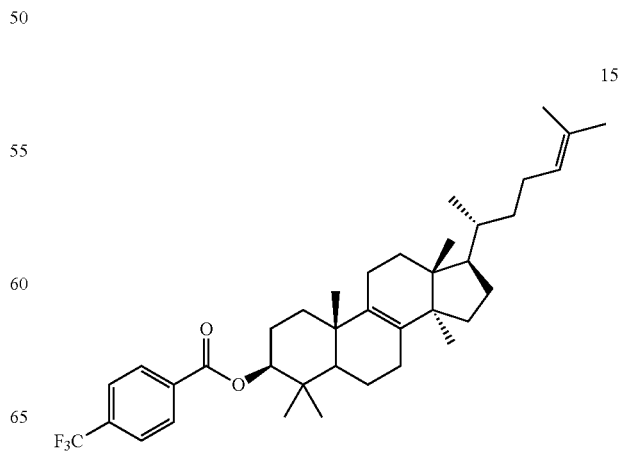

Synthesis Route:

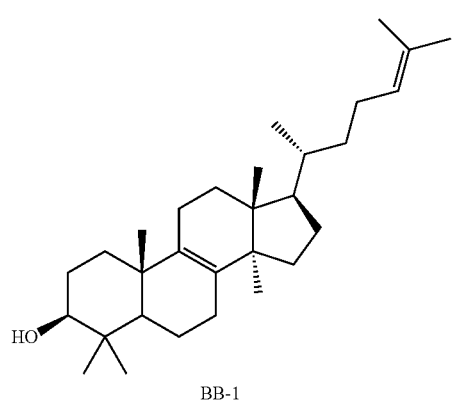

BB-1

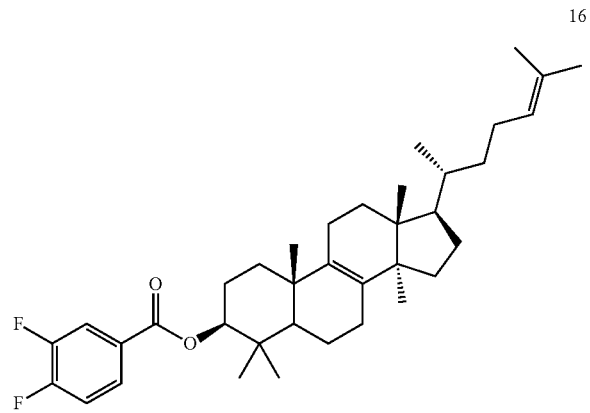 [SMILES: CC(C)=CCC[C@@H](C)[C@H]1CC[C@@]2(C)C3=C(CC[C@]12C)[C@@]1(C)CC[C@H](OC(=O)c2ccc(F)c(F)c2)C(C)(C)C1CC3]

15

Step 1: Synthesis of Compound 15

Compound 15 was obtained according to step 1 in embodiment 2. $^1$H NMR (CHLOROFORM-d, 400 MHz): δ=8.08 (d, J=8.0 Hz, 2H), 7.64 (d, J=8.5 Hz, 2H), 5.04 (br t, J=7.0 Hz, 1H), 4.68-4.74 (m, 1H), 1.75-2.04 (m, 8H), 1.60-1.73 (m, 7H), 1.37-1.55 (m, 7H), 1.02-1.37 (m, 7H), 0.98 (d, J=5.0 Hz, 6H), 0.81-0.90 (m, 9H), 0.64 ppm (s, 3H).

$^{19}$F NMR (CHLOROFORM-d, 377 MHz): δ=−63.06 ppm (br s, 3F).

Embodiment 16

Synthesis Route:

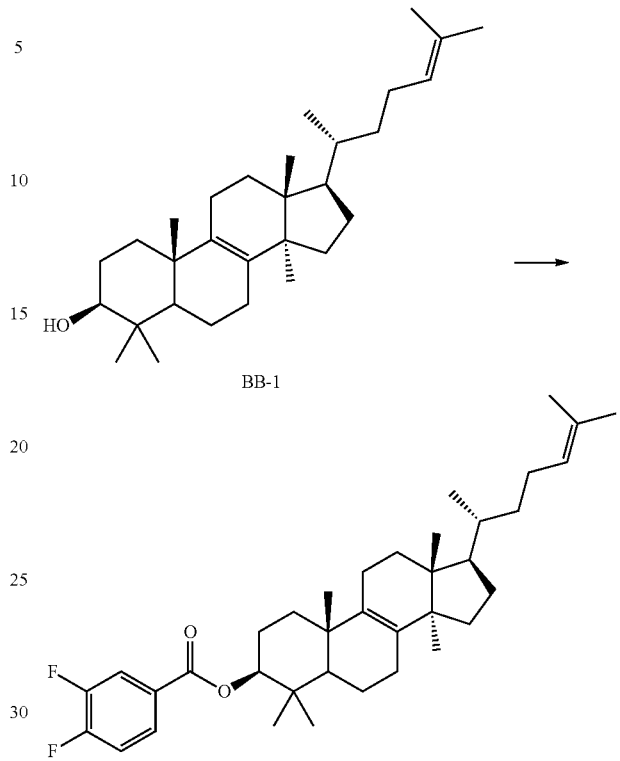

Step 1: Synthesis of Compound 16

Compound 16 was obtained according to step 1 in embodiment 2. $^1$H NMR (CHLOROFORM-d, 400 MHz): δ=7.72-7.81 (m, 2H), 7.11-7.19 (m, 1H), 5.03 (br t, J=7.0 Hz, 1H), 4.63-4.74 (m, 1H), 1.60-2.04 (m, 16H), 1.40-1.56 (m, 7H), 1.04-1.35 (m, 6H), 0.97 (d, J=9.0 Hz, 6H), 0.81-0.89 (m, 9H), 0.63 ppm (s, 3H).

$^{19}$F NMR (CHLOROFORM-d, 377 MHz): δ=−150.84-103.14 ppm (m, 1F).

Bioactivity Assay

Test embodiment 1: study of ophthalmic drug penetration and drug conversion to lanosterol in vivo In this study, New Zealand white rabbits (body weight was more than 2 kg, age was more than 12 weeks) were used as experimental animals. Each compound was studied with two New Zealand white rabbits. Each rabbit was instilled with 50 L eye drops in each eyes three eyes were used to collect aqueous humor samples and one eye was used as a backup. The formula of the eye drops was 1.2% hydroxypropyl methylcellulose (E5 size), 20.5% poloxamer (P407 size), 1.6% poloxamer (P188 size), the concentration of the compound was 5 mM, and the eye drops was a homogeneous suspension. After the eye drops was dripped into the rabbit's eyes, the anterior aqueous humor was collected at 0.5, 2, 4 and 6 hours after administration. The volume of each sample was not more than 50 μL. Each animal was given mild anesthesia before collecting samples. Three samples were collected at every time point. The collected aqueous humor samples were stored in dry ice immediately after collection or stored in a refrigerator at −80±10° C. After the sample collection, the animals were euthanized. The concentration of the compound in each sample was determined using a triple quadrupole mass spectrometer (API 4000). Tables 1 and 2 showed the DMPK assay in vivo; Tables 3 to 9 showed the drug concentration in the aqueous humor after compound lanosterol (parent drug) and the prodrug compound were dripped into eyes (250 nM per eye).

The results indicated that both lanosterol itself and its prodrug compound of the present invention could penetrate into the aqueous humor from the cornea or through other routes; and the prodrug compound could be converted into the parent drug lanosterol during the infiltration process and exhibited a higher concentration and exposure of lanosterol in the aqueous humor.

TABLE 1 the DMPK assay in vivo

| Compound name | Compound 1, 4, 8, 9, 10, 12 and lanosterol | | | |
|---|---|---|---|---|
| Liquid chromatography method | | | | |
| Mobile phase A | A solution of water and acetonitrile (the volume ratio is 95:5) containing 0.025% formic acid, 1 mmol of ammonium acetate buffer salt | | | |
| Mobile phase B | A solution of acetonitrile and water (the volume ratio 95:5) containing 0.025% formic acid, 1 mmol ammonium acetate buffer salt | | | |
| Chromatographic column | ACQUITY UPLC ® protein BEH 300A C4 1.7 µm 2.1 × 50 mm | | | |
| | Flow rate (µL/min) | A (%) | B (%) | |
| Gradient | 500 to 600 | 2 to 80 | 98 to 20 | |
| Mass spectrometry method | | | | |
| Ion source | APCI or ESI | | | |
| Scan mode | Multipolar ion monitoring | | | |
| Polarity | Positive ions | | | |
| Compound name | Ion pair | Retention time (min) | Declustering potential (eV) | Collision energy (eV) |
| Compound 1 | 668.4/200.2 | 1.62 | 50 | 56 |
| Compound 4 | 409.3/109.1 | 2.03 | 55 | 30 |
| Compound 8 | 409.3/109.1 | 2.05 | 50 | 38 |
| Compound 9 | 409.3/121.0 | 1.82 | 65 | 38 |
| Compound 10 | 409.3/135.4 | 1.79 | 55 | 38 |
| Compound 12 | 409.4/191.2 | 1.96 | 50 | 28 |
| Lanosterol | 409.4/149.1 | 1.48 | 50 | 38 |

TABLE 2 gradient of liquid chromatography method for DMPK of lanosterol and compound 8 in vivo

| Flow rate | Gradient | | |
|---|---|---|---|
| | Time (minute) | A (%) | B (%) |
| 500 µL/min | start | 80.0 | 20.0 |
| | 0.30 | 70.0 | 30.0 |
| | 1.20 | 20.0 | 80.0 |
| | 2.00 | 2.0 | 98.0 |
| | 2.30 | 2.0 | 98.0 |
| | 2.31 | 80.0 | 20.0 |
| | 2.40 | 80.0 | 20.0 |

TABLE 3 the average concentration of the sample in the aqueous humor (nM) after 250 nmol lanosterol was dripped into each eye of New Zealand white rabbit

| | Eye drops compound name<br>Lanosterol (parent drug)<br>Test compound name<br>Lanosterol (parent drug) |
|---|---|
| Time (hour) | Average concentration (nM) |
| 0.5 | 106* |
| 2 | 496 |
| 4 | 300 |
| 6 | 225 |
| AUC (nM · h) | 1779 |

*BQL: below quantitation limit, AUC: exposure amount.

TABLE 4 the average concentration of the sample in the aqueous humor (nM) after 250 nmol compound 1 was dripped into each eye of New Zealand white rabbit

| | Eye drops compound name<br>Compound 1 (prodrug)<br>Test compound name | |
|---|---|---|
| Time (hour) | Compound 1 Average concentration (nM) | Lanosterol Average concentration (nM) |
| 0.5 | 7.5 | BQL |
| 2 | 8.6 | BQL |
| 6 | BQL | 15.6 |

*BQL: below quantitation limit

TABLE 5 the average concentration of the sample in the aqueous humor (nM) after 250 nmol compound 4 was dripped into each eye of New Zealand white rabbit

| | Eye drops compound name<br>Compound 4 (prodrug)<br>Test compound name | |
|---|---|---|
| Time (hour) | compound 4 Average concentration (nM) | Lanosterol Average concentration (nM) |
| 0.5 | BQL | 278 |
| 2 | BQL | 326 |
| 4 | BQL | 67.7 |
| 6 | BQL | 73.6 |

*BQL: below quantitation limit

TABLE 6 the average concentration of the sample in the aqueous humor (nM) after 250 nmol compound 8 was dripped into each eye of New Zealand white rabbit

| | Eye drops compound name<br>Compound 8 (prodrug)<br>Test compound name | |
|---|---|---|
| Time (hour) | Compound 8 Average concentration (nM) | Lanosterol Average concentration (nM) |
| 0.5 | 41.0 | 471 |
| 2 | 33.3 | 478 |

TABLE 6-continued

| | | |
|---|---|---|
| 4 | 25.5 | 403 |
| 6 | BQL | 586 |
| AUC (nM · h) | 124 | 2700 |

*BQL: below quantitation limit, AUC: exposure amount.

TABLE 7 the average concentration of the sample in the aqueous humor (nM) after 250 nmol compound 9 was dripped into each eye of New Zealand white rabbit

| | Eye drops compound name Compound 9 (prodrug) Test compound name | |
|---|---|---|
| Time (hour) | Compound 9 Average concentration (nM) | Lanosterol Average concentration (nM) |
| 0.5 | BQL | 171 |
| 2 | BQL | 879 |

*BQL: below quantitation limit

TABLE 8 the average concentration of the sample in the aqueous humor (nM) after 250 nmol compound 10 was dripped into each eye of New Zealand white rabbit

| | Eye drops compound name Compound 10 (prodrug) Test compound name | |
|---|---|---|
| Time (hour) | Compound 10 Average concentration (nM) | Lanosterol Average concentration (nM) |
| 0.5 | BQL | 405 |
| 2 | 37.9 | 1482 |

*BQL: below quantitation limit

TABLE 9 the average concentration of the sample in the aqueous humor (nM) after 250 nmol compound 12 was dripped into each eye of New Zealand white rabbit

| | Eye drop compound name Compound 12 (prodrug) Test compound name | |
|---|---|---|
| Time (hour) | Compound 12 Average concentration (nM) | Lanosterol Average concentration (nM) |
| 0.5 | 60 | 422 |
| 2 | 15.6 | 308 |
| 4 | BQL | 165 |
| 6 | BQL | 210 |
| AUC (nM · h) | BQL | 1480 |

*BQL: below quantitation limit, AUC: exposure amount.

Test Embodiment 2: pharmacodynamic study of lanosterol eye drops and its prodrug on sodium selenite-induced cataract of neonatal new zealand rabbits model 1. Experimental Animal P7 days old neonatal New Zealand rabbits, normal grade, and 5 young rabbits per litter were breast-fed with a mother rabbit.

2. Grouping and Processing

The experimental young rabbits were randomly divided into 5 groups with 5 rabbits per group.

1) Normal control group (NC): in the P10 day, young rabbits were injected subcutaneously with 0.25 mL physiological saline from the neck, and were not administered after the P15 day.

2) Model control group (MC): in the P10 day, young rabbits were injected subcutaneously with sodium selenite solution (in physiological saline) at 20 μmol/kg body weight, and after the P15 day, drug-free blank eyes drops was dripped into the right eye 3 times every day for 42 days.

3) Positive control group (PC): in the P10 day, young rabbits were injected subcutaneously with sodium selenite solution (in physiological saline) at 20 μmol/kg body weight, and after the P15 day, kary uni eye drops (Santen Pharmaceutical Co., Ltd in Japan) was dripped into the right eye 3 times every day for 42 days.

4) Lanosterol eye drops treatment group (LT): in the P10 day, young rabbits were injected subcutaneously with sodium selenite solution (in physiological saline) at 20 μmol/kg body weight, and after the P15 day, lanosterol eye drops was dripped into the right eye 3 times every day for 42 days.

5) Lanosterol prodrug 026 eye drops treatment group (026): in the P10 day, young rabbits were injected subcutaneously with sodium selenite solution (in physiological saline) at 20 μmol/kg body weight, and after the P15 day, lanosterol prodrug 026 eye drops was dripped into the right eye 3 times every day for 42 days.

3. Experimental Test

1) Slit lamp photography: sodium selenite-induced neonatal New Zealand rabbits in each group were observed with slit lamp before the administration, and 7 days, 14 days, 21 days and 42 days after the administration respectively;

2) Lens transparency test in vitro: on the last day, the animal's eyeball was dissected, the lens containing the capsule was completely separated, and the lens was placed on a grid paper (2.12×2.12 mm). The photographs showed the sharpness of the grid photographed through the lens.

3) Glutathione peroxidase (GSH-PX) activity assay: GSH-PX activity of the isolated rabbit lens in each group was determined by the method provided in the specification of GSH-PX activity detection kit (Nanjing Jiancheng Bio-engineering Institute). The experimental data was analyzed by One-Way ANOVA with SPSS statistical software. The LSD method was used to compare the groups, and the statistical difference level was $p<0.05$.

4. Experimental Result

1) Slit lamp observation: FIG. 1 showed that sodium selenite could induce cataract in neonatal New Zealand rabbit lens. Slit lamp observation showed the cataract symptoms were significantly reduced after lanosterol prodrug 026 eye drops was administered for 42 days (FIG. 1-I) compared with pre-dose (FIG. 1-J). The cataract symptoms did not change significantly before and after the administration of kary uni eye drops (FIG. 1-E, 1-F) and lanosterol eye drops (FIG. 1-G, 1-H).

Figure 2:
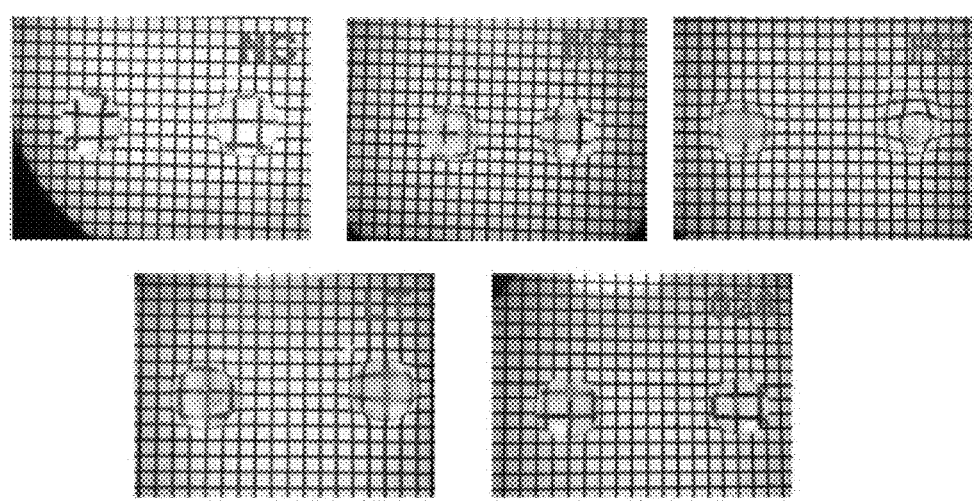
FIG. 2 is the comparison of lens transparency of sodium selenite-induced neonatal New Zealand rabbit cataract model in each group in vitro after 42 days of administration. NC: normal control group; MC: model control group; PC: positive control group; LT: lanosterol eye drops treatment group; 026: lanosterol prodrug 026 eye drops treatment group. Grid is 2.12×2.12 mm.

2) Lens transparency test in vitro: FIG. 2 showed the lens transparency of neonatal New Zealand rabbits with sodium selenite-induced cataract in each group after 42 days of administration. On the left side of each photograph was the left eye lens (left eye was not administered as a self-control), and on the right was the right eye lens (the right eye was administered according to grouping). After 42 days of administration of lanosterol prodrug 026 eye drops, the transparency of the right eye lens was significantly higher than that of the left eye, and also significantly higher than that of the MC group, but it was still lower than that of the NC group. There was no significant change in lens transparency after the right eye was administrated in the LT group.

Figure 3:
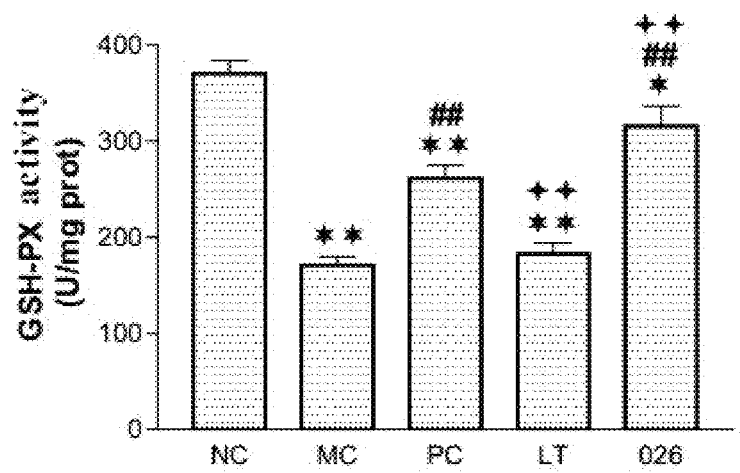
FIG. 3 is the comparison of lens glutathione peroxidase (GSH-PX) activity of sodium selenite-induced neonatal New Zealand rabbit cataract model after 42 days of administration. NC: normal control group; MC: model control group; PC: positive control group; LT: lanosterol eye drops treatment group; 026: lanosterol prodrug 026 eye drops treatment group. V.S NC: * * stands for $p<0.01$, * stands for $p<0.05$; V.S MC: ## stands for $p<0.01$, # stands for $p<0.05$; V.S PC: ++ stands for $p<0.01$, + stands for $p<0.05$.

3) GSH-PX activity assay: after 42 days of administration, the result of the GSH-PX activity of the lens in each group showed (see FIG. 3) that after subcutaneous injection of sodium selenite, the activity of GSH-PX in the lens of rabbit eyes was significantly reduced and there was a statistical difference ($p<0.01$) compared to the NC group. The lanosterol prodrug 026 eye drops and the positive control drug kary uni eye drops could increase the GSH-PX activity of the lens, and there was a statistical difference compared to the MC group ($p<0.01$), and the improvement effect of 026 is better than that of kary uni ($p<0.01$). The effect of lanosterol eye drops on the activity of lens GSH-PX was significantly lower than that of 026 and kary uni, and there was no statistical difference compared to the MC group ($p>0.05$).

5. Conclusion

The above results indicated that the lanosterol prodrug 026 eye drops could alleviate the cataract symptoms of neonatal New Zealand rabbits induced by sodium selenite and improve lens transparency and lens GSH-PX activity.

Test embodiment 3: pharmacodynamic study of lanosterol eye drops and its prodrug on ultraviolet-induced neonatal New Zealand rabbits cataract model 1. Experimental Animal Adult New Zealand rabbits 2.0-2.5 kg, normal grade, male and female, a total of 25.

Grouping and Processing

The experimental rabbits were randomly divided into 5 groups with 5 rabbits per group.

1) Normal control group (NC): normal feeding, no drug administration.

2) Model control group (MC): 313 nm UV irradiation for 24 hours to make model, then drug-free blank eye drops was dripped to the right eye 3 times every day for 42 days.

3) Positive control group (PC): 313 nm UV irradiation for 24 hours to make model, then kary uni eye drops (Santen Pharmaceutical Co., Ltd in Japan) was dripped into the right eye 3 times every day for 42 days.

4) Lanosterol eye drops treatment group (LT): 313 nm UV irradiation for 24 hours to make model, then lanosterol eye drops was dripped into the right eye 3 times every day for 42 days.

5) Lanosterol prodrug 026 eye drops treatment group (026): 313 nm UV irradiation for 24 hours to make model, then the lanosterol prodrug 026 eye drops was dripped into the right eye 3 times every day for 42 days.

3. Experimental Test

1) Slit lamp photography: each group was observed with slit lamp before the administration, and 7 days, 14 days, 21 days and 42 days after the administration respectively;

2) lens transparency test in vitro: on the last day, the animal's eyeball was dissected, the lens containing the capsule was completely separated, and the lens was placed on a grid paper (2.12×2.12 mm). The photographs showed sharpness of the grid photographed through the lens.

3) Glutathione peroxidase (GSH-PX) activity assay: GSH-PX activity of the isolated rabbit lens in each group was determined by the method provided in the specification of GSH-PX activity detection kit (Nanjing Jiancheng Bioengineering Institute). The experimental data was analyzed by One-Way ANOVA with SPSS statistical software. The LSD method was used to compare the groups, and the statistical difference level was $p<0.05$.

4. Experimental Result

Figure 4:
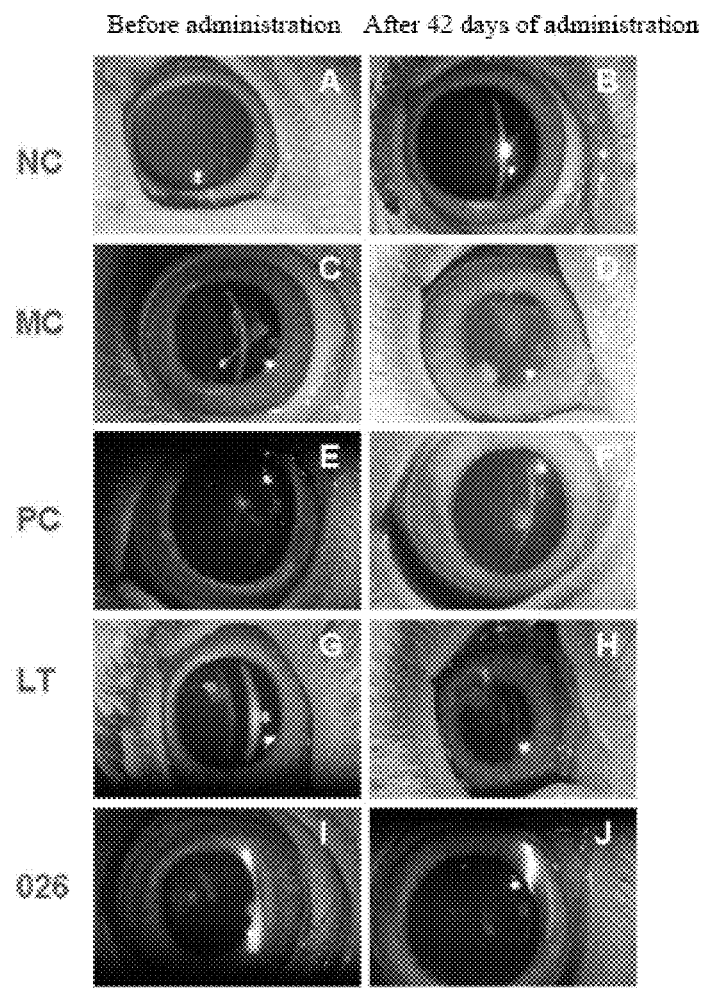
FIG. 4 is the effect of lanosterol and its prodrug 026 eye drops on ultraviolet-induced New Zealand rabbit cataract model observed by slit lamp. NC: normal control group; MC: model control group; PC: positive control group; LT: lanosterol eye drops treatment group; 026: lanosterol prodrug 026 eye drops treatment group.

1) Slit lamp observation: FIG. 4 showed that ultraviolet could induce cataract in New Zealand rabbit lens. Slit lamp observation showed the cataract symptoms were significantly reduced after lanosterol prodrug 026 eye drops was administered for 42 days (FIG. 4-I) compared with pre-dose (FIG. 4-J). The cataract symptoms did not change significantly before and after the administration of kary uni eye drops (FIG. 4-E, 4-F) and lanosterol eye drops (FIG. 4-G, 4-H).

Figure 5:
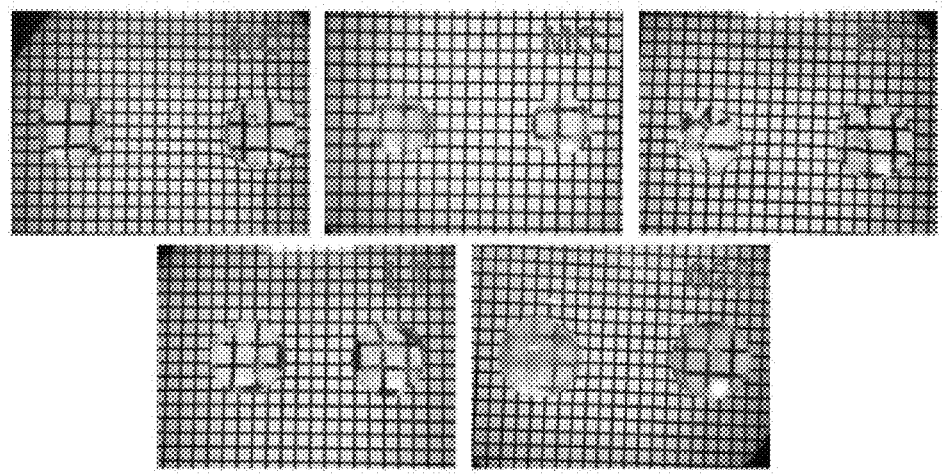
FIG. 5 is the comparison of lens transparency of ultraviolet-induced New Zealand rabbit cataract in each group in vitro after 42 days of administration. NC: normal control group; MC: model control group; PC: positive control group; LT: lanosterol eye drops treatment group; 026: Lanosterol prodrug 026 eye drops treatment group. Grid is 2.12×2.12 mm.

2) lens transparency test in vitro: FIG. 5 showed the lens transparency of New Zealand rabbits with cataract induced by ultraviolet in each group after 42 days of administration. On the left side of each photograph was the left eye lens (left eye was not administered as a self-control), and on the right was the right eye lens (the right eye was administered according to grouping). After 42 days of administration of lanosterol prodrug 026 eye drops, the transparency of the right eye lens was significantly higher than that of the left eye, and also significantly higher than that of the MC group, but it was still lower than that of the NC group. There was no significant change in lens transparency after the right eye was administrated in the LT group.

Figure 6:
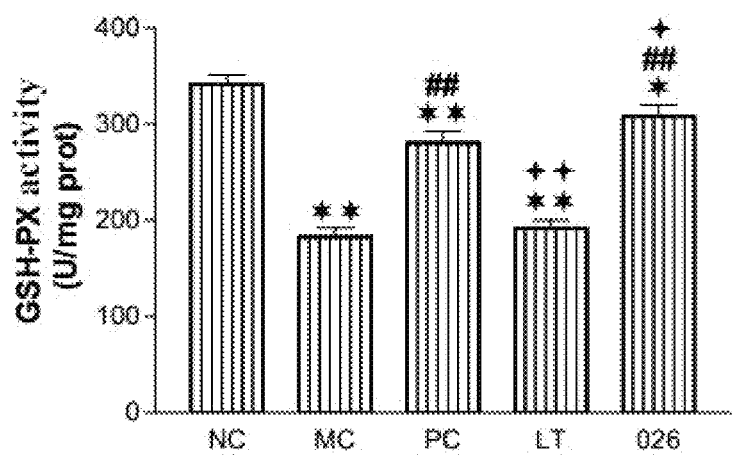
FIG. 6 is the comparison of lens glutathione peroxidase (GSH-PX) activity of ultraviolet-induced neonatal New Zealand rabbit cataract in each group after 42 days of administration. NC: normal control group; MC: model control group; PC: positive control group; LT: lanosterol eye drops treatment group; 026: lanosterol prodrug 026 eye drops treatment group. V.S NC: ** stands for $p<0.01$, * stands for $p<0.05$; V.S MC: ## stands for $p<0.01$, # stands for $p<0.05$; V.S PC: ++ stands for $p<0.01$, + stands for $p<0.05$.

3) GSH-PX activity assay: after 42 days of administration, the GSH-PX activity of the lens in each group showed (see FIG. 6) that after UV irradiation, the activity of GSH-PX in the lens of rabbit eyes was significantly reduced and there was a statistical difference compared to the NC group ($p<0.01$ or $p<0.05$). The lanosterol prodrug 026 eye drops and the positive control drug kary uni eye drops could increase the GSH-PX activity of the lens, and there was a statistical difference compared to the MC group ($p<0.01$), and the improvement effect of 026 was better than that of kary uni ($p<0.05$). The effect of lanosterol eye drops on the activity of lens GSH-PX was significantly lower than that of 026 and kary uni, and there was no statistical difference compared to the MC group ($p>0.05$).

5. Conclusion

The above results indicated that the lanosterol prodrug 026 eye drops could alleviate the cataract symptoms of New Zealand rabbits induced by UV irradiation, and improve lens transparency and lens GSH-PX activity.

What is claimed is:

1. A compound represented by formula (II), a pharmaceutically acceptable salt or an isomer thereof,

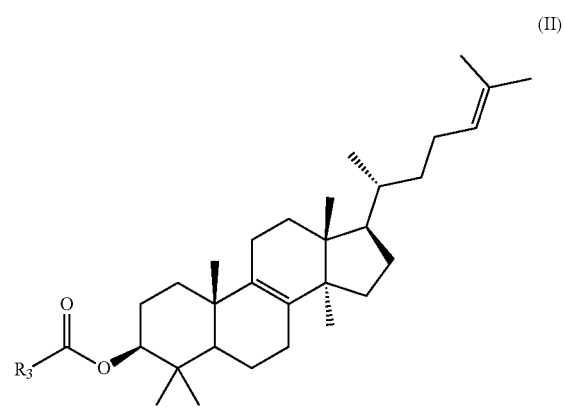

wherein, $R_3$ is selected from the group consisting of 6-10-membered aryl and 5-10-membered heteroaryl, each of which is optionally substituted with 1 or 3 R, but R₃ is not unsubstituted phenyl and

[structure: pyridin-4-yl];

each of R is independently NO₂, OH, or CH₃—C(=O)—O—;
the "hetero" in the 5-10-membered heteroaryl is independently selected from the group consisting of —NH—, N, —O— and —S—;
in any of the above case, the number of heteroatom or heteroatom group is independently 1, 2 or 3.

2. The compound, the pharmaceutically acceptable salt or the isomer thereof according to claim 1, wherein, R₃ is selected from the group consisting of phenyl, thienyl, pyridyl, quinolyl, pyrimidyl, isoxazolyl and 1,2,4-oxadiazolyl, each of which is optionally substituted with 1 or 3 R, but R₃ is not unsubstituted phenyl and

[structure: pyridin-4-yl];

3. The compound, the pharmaceutically acceptable salt or the isomer thereof according to claim 2, wherein, R₃ is selected from the group consisting of

[structures: pyridin-4-yl, phenyl, quinolin-3-yl, pyrimidin-5-yl, isoxazol-5-yl, and 1,2,4-oxadiazol-3-yl], each of which is optionally substituted with 1 or 3 R, but R₃ is not unsubstituted phenyl.

4. The compound, the pharmaceutically acceptable salt or the isomer thereof according to claim 3, wherein, R₃ is

[structures: pyridin-3-yl, 4-nitrophenyl, quinolin-3-yl, pyrimidin-5-yl, 2-hydroxyphenyl, 2-acetoxyphenyl, isoxazol-5-yl, or 1,2,4-oxadiazol-3-yl].

5. A compound, a pharmaceutically acceptable salt or an isomer thereof, which is selected from the group consisting of:

[four triterpenoid ester structures with pyridine-3-carboxylate, 4-nitrobenzoate, quinoline-3-carboxylate, and pyrimidine-5-carboxylate groups]

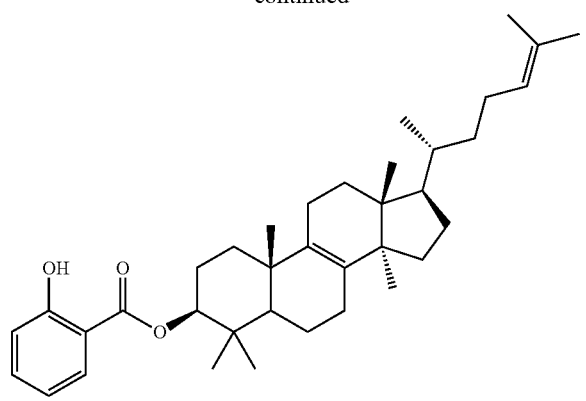
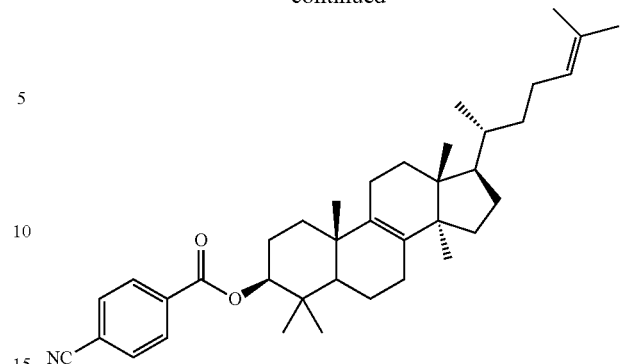
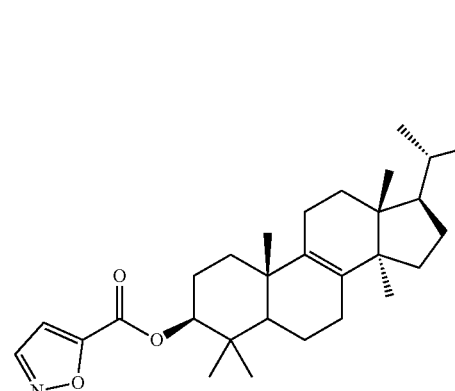
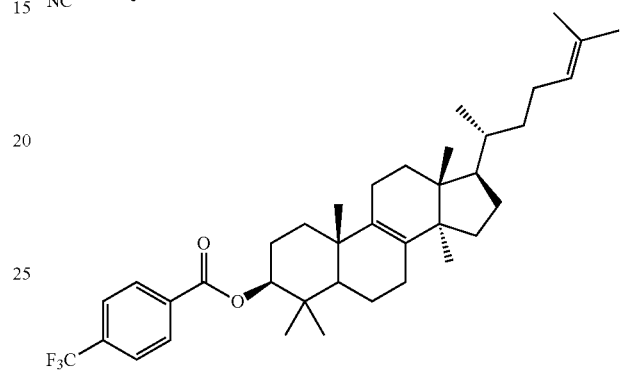
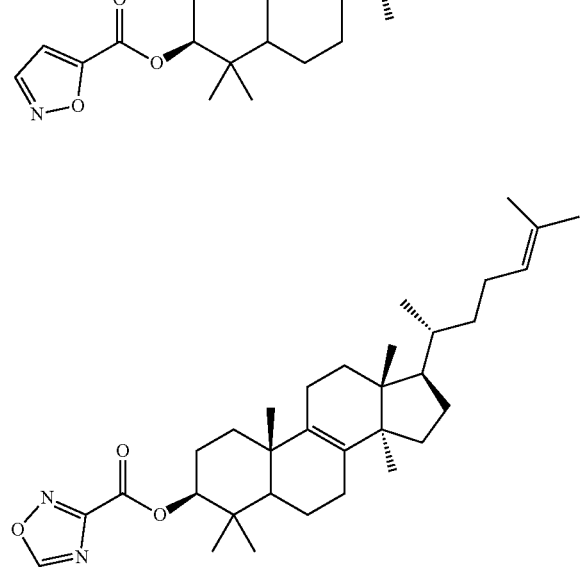
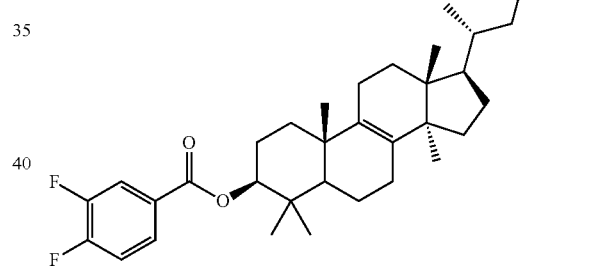

and

6. A pharmaceutical composition comprising a therapeutically effective amount of the compound or the pharmaceutically acceptable salt thereof according to claim 1 as active ingredient, and a pharmaceutically acceptable carrier.

7. A method for treating a cataract in a subject in need thereof, comprising administering an effective amount of the compound or the pharmaceutically acceptable salt according to claim 1 to the subject.

8. The method according to claim 7, wherein, the cataract is treated by administering eye drops.

9. A method for treating a cataract in a subject in need thereof, comprising administering an effective amount of the pharmaceutical composition according to claim 6 to the subject.

10. A pharmaceutical composition comprising a therapeutically effective amount of the compound or the pharmaceutically acceptable salt thereof according to claim 5 as active ingredient, and a pharmaceutically acceptable carrier.

11. A method for treating a cataract in a subject in need thereof, comprising administering an effective amount of the compound or the pharmaceutically acceptable salt according to claim 5 to the subject.

12. The method according to claim 11, wherein, the cataract is treated by administering eye drops.

13. A method for treating a cataract in a subject in need thereof, comprising administering an effective amount of the pharmaceutical composition according to claim 10 to the subject.

* * * * *

UNITED STATES PATENT AND TRADEMARK OFFICE
CERTIFICATE OF CORRECTION

PATENT NO. : 10,738,076 B2
APPLICATION NO. : 16/346111
DATED : August 11, 2020
INVENTOR(S) : Yizhi Liu et al.

Page 1 of 1

It is certified that error appears in the above-identified patent and that said Letters Patent is hereby corrected as shown below:

In the Claims

Column 57, Claim 3, Line 35, " 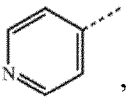 " should be -- 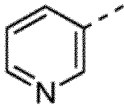 --.

Column 59, Claim 5, Line 55, " 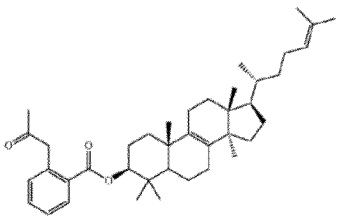 " should be -- 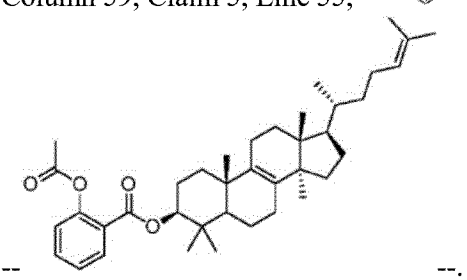 --.

Signed and Sealed this
Fifteenth Day of December, 2020

Andrei Iancu
*Director of the United States Patent and Trademark Office*